United States Patent [19]
Yamamoto et al.

[11] Patent Number: 4,874,924
[45] Date of Patent: Oct. 17, 1989

[54] PTC HEATING DEVICE

[75] Inventors: Shinobu Yamamoto; Fumitoshi Hoshide, both of Hiroshima; Michikazu Takeuchi, Tokyo; Shou Kotani, Tokyo; Sumihiro Yasuda, Tokyo, all of Japan

[73] Assignee: TDK Corporation, Tokyo, Japan

[21] Appl. No.: 183,710

[22] Filed: Apr. 19, 1988

[30] Foreign Application Priority Data

Apr. 21, 1987 [JP] Japan .................................. 60163
Nov. 16, 1987 [JP] Japan .................................. 174598

[51] Int. Cl.⁴ ........................... H05B 3/14; A61L 9/03
[52] U.S. Cl. ...................................... 219/274; 219/275
[58] Field of Search ............... 219/274, 271, 276, 504, 219/505, 521, 530, 540, 206, 237, 301; 123/549, 557; 338/22 R

[56] References Cited

U.S. PATENT DOCUMENTS

| | | | |
|---|---|---|---|
| 3,976,854 | 8/1976 | Ishikawa | 338/22 R |
| 3,996,447 | 12/1976 | Bouffard | 219/505 |
| 4,334,141 | 6/1982 | Roller | 338/22 R |
| 4,371,778 | 2/1983 | Meixner | 219/301 |
| 4,407,254 | 10/1983 | Kato | 123/549 |
| 4,447,706 | 5/1984 | Eder | 123/557 |
| 4,489,232 | 12/1984 | Wada | 219/206 |
| 4,544,829 | 10/1985 | Adachi | 219/237 |
| 4,700,050 | 10/1987 | Hennuy | 338/22 R |
| 4,728,779 | 3/1988 | Kotani | 219/540 |

FOREIGN PATENT DOCUMENTS

| | | | |
|---|---|---|---|
| 2804749 | 8/1979 | Fed. Rep. of Germany | 219/301 |
| 2804804 | 8/1979 | Fed. Rep. of Germany | 219/301 |
| 2143708 | 2/1985 | United Kingdom | 123/549 |

*Primary Examiner*—Teresa J. Walberg
*Attorney, Agent, or Firm*—Helfgott & Karas

[57] ABSTRACT

A PTC heating device is adapted to be used as a heat source for an electric vaporizer which is adapted to heat liquid medicine, e.g., liquid insecticide, aromatic liquid, or the like, to vaporize it. The PTC heating device includes a casing in which an electrode structure including at least one PTC thermistor having electrodes arranged on both surfaces thereof and two electrode members interposing the PTC thermistor therebetween is received. The PTC heating device further includes a heat-radiating member mounted through a heat-conducting member with respect to the casing and for heating an absorber having sucked up liquid medicine from a reservoir having the liquid medicine contained therein to vaporize the liquid medicine. One of the electrodes of the PTC thermistor is in close contact with a flat surface of the heat-conducting member through one of two electrode members, so that heat generated at the PTC thermistor is efficiently transmitted to the heat-radiating member through the heat-conducting member.

13 Claims, 15 Drawing Sheets

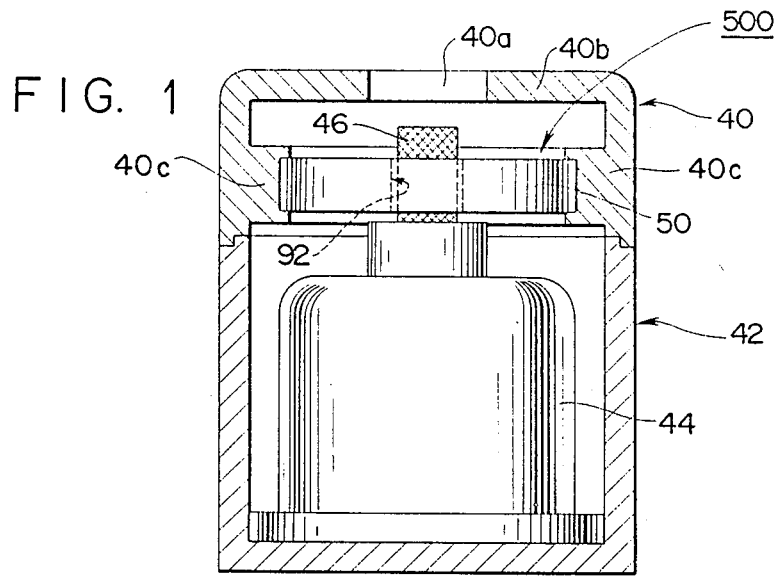
F I G. 1

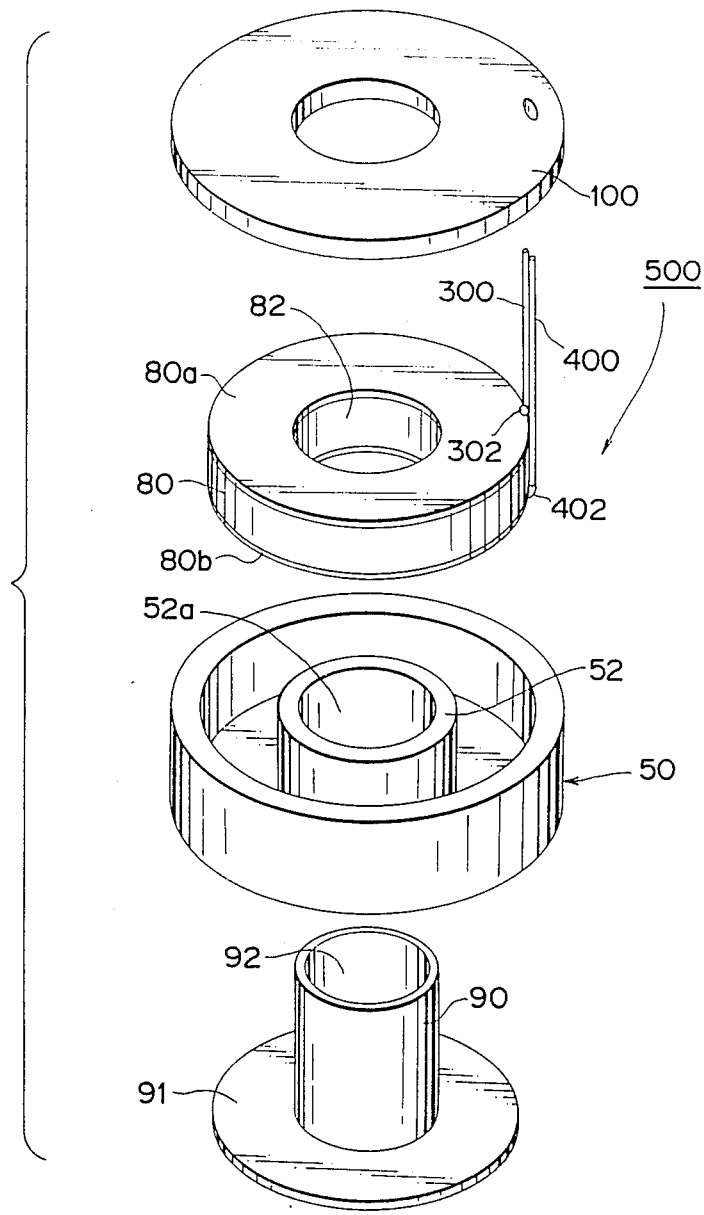

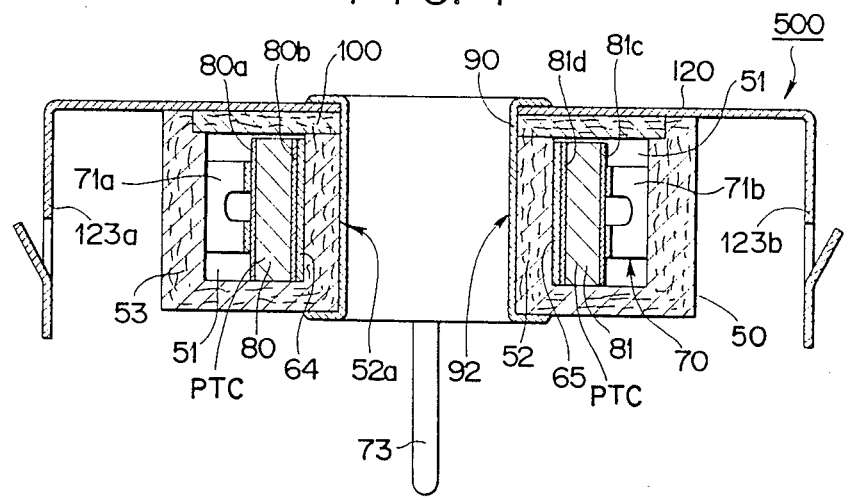
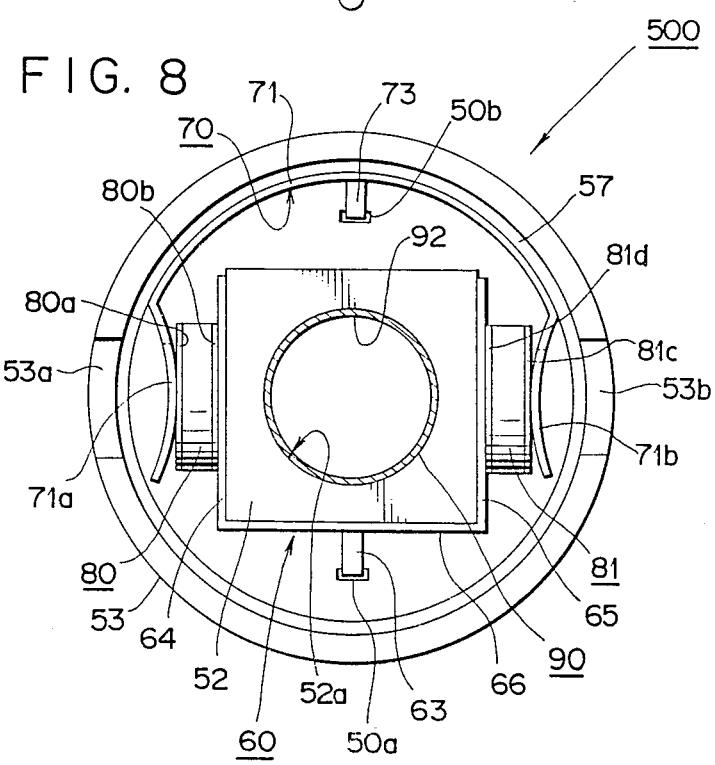

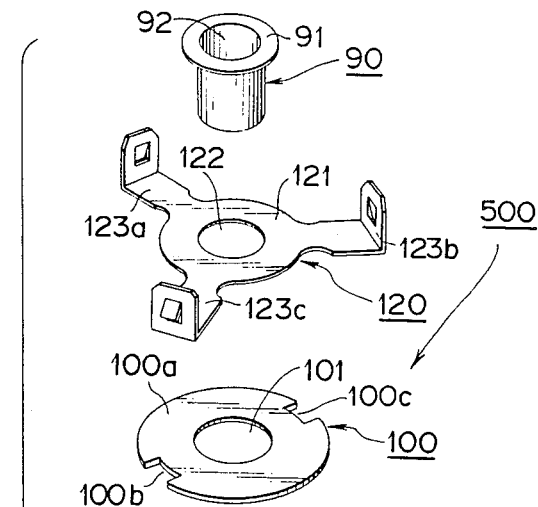
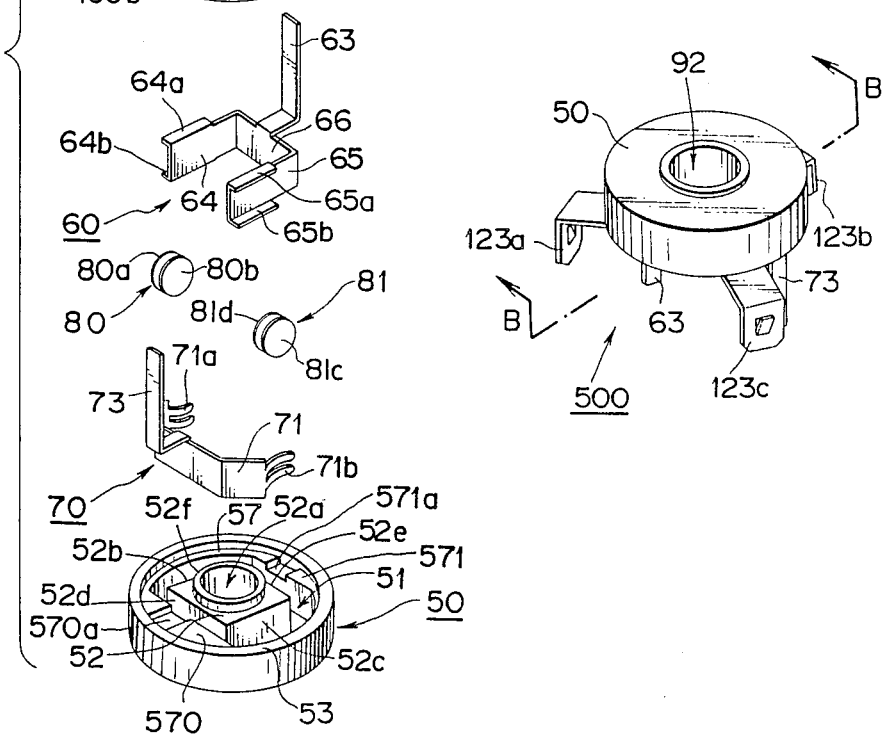
FIG. 9
FIG. 10

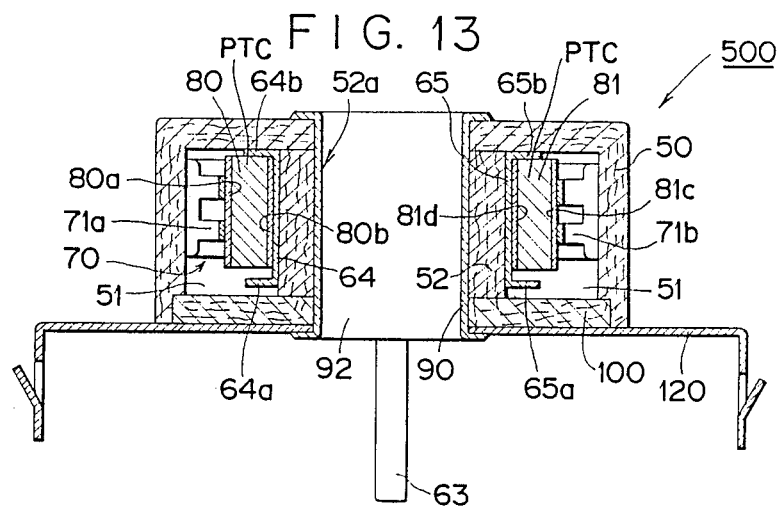
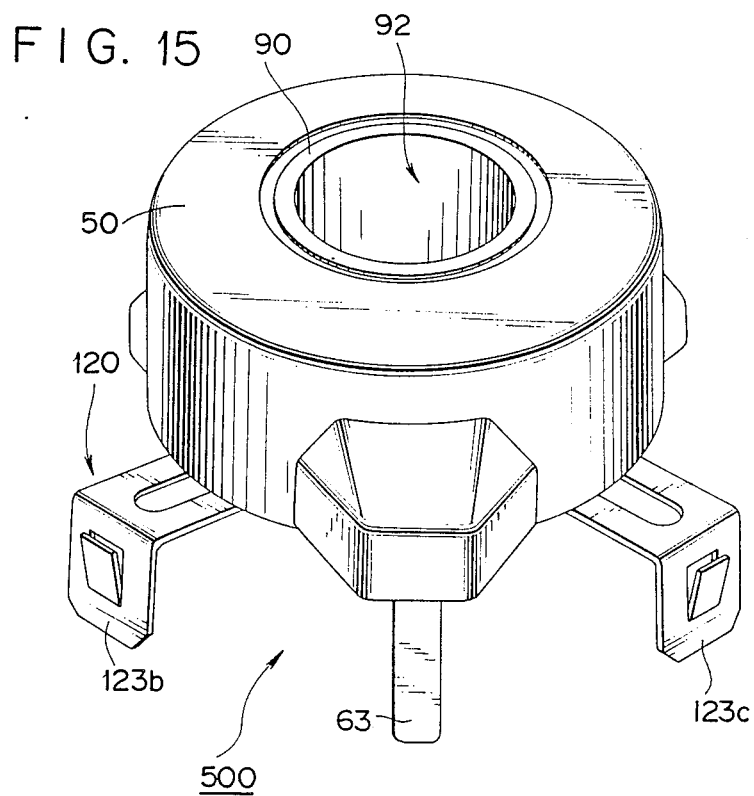

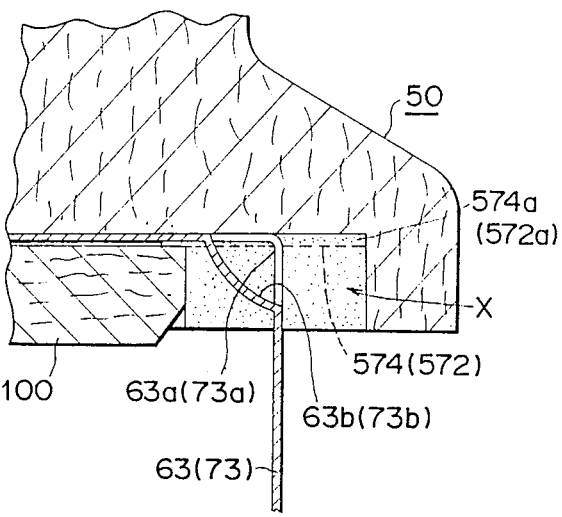
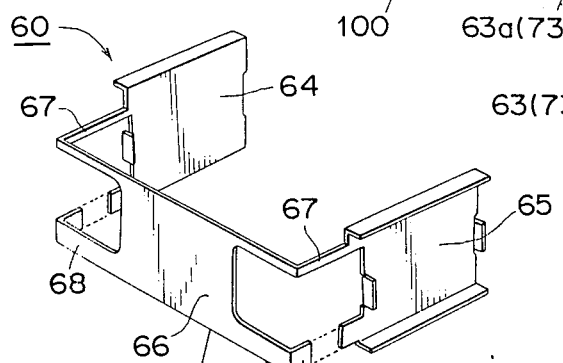
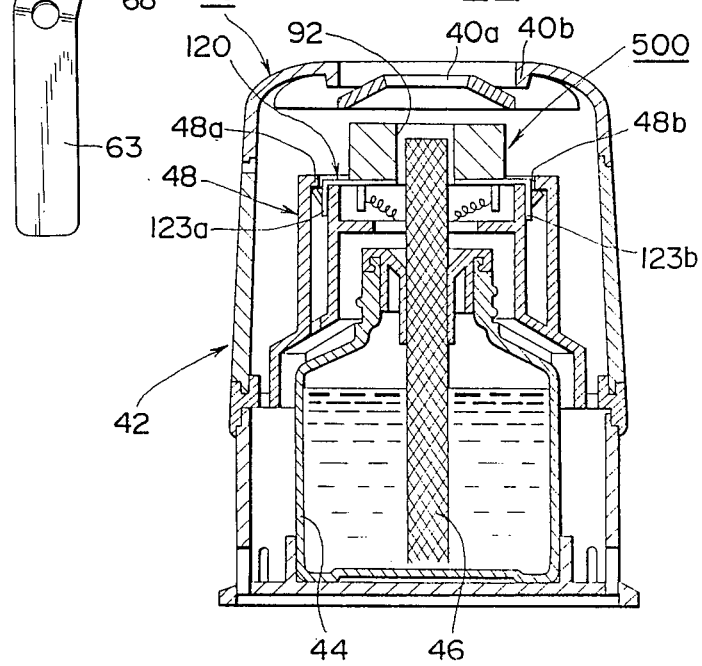

PTC HEATING DEVICE

BACKGROUND OF THE INVENTION

1. Field of the Invention

This invention relates to a positive temperature coefficient (hereinafter referred to as "PTC") heating device, and more particularly to a PTC heating device which is adapted to be used as a heat source for an electric vaporizer which is adapted to heat liquid material, e.g., liquid insecticide, aromatic liquid, or the like, to vaporize it. Such electric vaporizer includes an electric mosquito destroyer, an electric vaporizer for heating aromatic liquid to vaporize it, and the like. As an example of such an electric vaporizer having a PTC heating device incorporated therein, an electric mosquito destroyer will be referred to in the following.

2. Description of the Prior Art

This type of electric mosquito destroyer generally comprises a reservoir having liquid insecticide contained therein, and an wick for sucking up the liquid insecticide from the reservoir, in which electric mosquito destroyer the liquid insecticide having been sucked up from the reservoir through the wick is adapted to be heated to vaporize. In the electric mosquito destroyer, a PTC thermistor which is capable of safely heating the liquid insecticide to reliably vaporize it is employed. The wick usually has a body which is made of fibrous material such as felt, or porous material.

Referring now to FIG. 1, this type of electric mosquito destroyer having a PTC heating device incorporated therein will be described more in detail in order to facilitate understanding of the present invention. The electric mosquito destroyer comprises upper and lower armoring cases 40 and 42 which are adapted to be fitted into each other, and a reservoir 44 having liquid insecticide contained therein, the reservoir 44 being housed in the lower armoring case 42. The upper armoring case 40 has a through-hole 40a formed at its upper wall 40b, and socket portions 40c integrally formed on an inner surface of its side wall. As described above, the electric mosquito destroyer further comprises the PTC heating device 500 which includes a casing 50 and a cylindrical heat-radiating member 90 (see FIG. 2) which is mounted with respect to the casing 50 as will later be described in detail. The PTC heating device 500 is mounted with respect to the upper armoring case 40 in a manner such that the casing 50 thereof is partially fitted in the respective socket portions 40c of the upper armoring case 40. In FIG. 1, a reference numeral 46 designates a wick for sucking up liquid insecticide from the reservoir 44, which wick has an elongated body made of fibrous material such as felt, or porous material as described above. The elongated wick 46 is inserted into the reservoir 44 through a mouth of the reservoir 44 to be immersed in the liquid insecticide contained in the reservoir 44, an upper end portion of which elongated wick 46 is projected from the mouth of the reservoir 44. The upper armoring case 40 having the PTC heating device 500 mounted with respect thereto and the lower armoring case 42 are fitted into each other in a manner such that the upper end portion of the elongated wick 46 is inserted through a longitudinal bore 92 (FIGS. 1 and 2) of the cylindrical heat-radiating member 90.

In the electric mosquito destroyer constructed as described above, when heat is generated at a PTC thermistor, which is incorporate in the PTC heating device 500 as will later be described in detail, to be transmitted to the heat-radiating member 90, the upper end portion of the wick 46 having sucked up liquid insecticide from the reservoir 44 is heated due to the heat which has been conducted to the heat radiating member 90, resulting in the liquid insecticide vaporizing. Thus, the vaporized insecticide is diffused out of the electric mosquito destroyer through the through-hole 40a of the upper armoring case 40.

Referring to FIG. 2, a conventional PTC heating device 500 comprises a PTC thermistor 80, an upper electrode plate 70 and a lower electrode plate 60 between which the PTC thermistor 80 is vertically interposed, a casing 50 having a recess 51 formed therein, and a cylindrical heat-radiating member 90.

The casing 50 is made of heat-resistant plastic material and comprises a body having the recess 51 and a cylindrical portion 52 serving as heat-conducting section which is formed integrally with the body so as to protrude upwardly from a substantially central portion of an outer bottom surface of the recess 51. The PTC thermistor 80 has a ring-like body and an upper electrode 80a and a lower electrode 80b on an upper and a lower surface of its body, respectively. The PTC thermistor 80 and the electrode plates 70 and 60 are received in the recess 51 of the casing 50 in a manner to be fitted on the cylindrical portion 52 of the casing 50 through their through-hole 82, through-hole 72 and through-hole 62, respectively. In FIG. 2, a reference number 100 designates a cover plate. The cover plate 100 is made of heat-resistant plastic material, has a through-hole 101, and is arranged on the upper electrode plate 70 in a manner such that its through-hole 101 is aligned with a longitudinal bore 52a of the cylindrical portion 52 of the casing 50 through its, thereby blocking up the recess 51 of the casing 50. The cylindrical heat-radiating member 90 is made of metal such as aluminum and provided at its one end with a flange 91. The heat-radiating member 90 is mounted with respect to the casing 50 in a manner to be inserted through the through-hole of the cover plate 100 and the longitudinal bore 52a of the cylindrical portion 52 of the casing 50 to be riveted over the outer bottom surface of the casing 50 at the other end thereof.

The conventional PTC heating device constructed as described above has various problems as will be described hereinafter.

As described above, the conventional PTC heating device 500 includes the ring-shaped PTC thermistor 80. In the manufacture of the ring-shaped PTC thermistor, it has been the practice to form the electrodes by electrolessly plating the entire surface of ring-shaped substance for the PTC thermistor with, e.g., nickel and then heat-treating same. Thereafter, nickel film on an inner wall surrounding a through-hole of the ring-shaped substance is removed by, for example, grinding. The grinding operation is, however, highly troublesome, thus requiring substantial time for the removal of the nickel film. Therefore, the ring-shaped PTC thermistor has become expensive. As an alternative, removal of the nickel film from the inner wall may be carried out by chemical etching. This, however, causes the ring-shaped substance and electrodes formed on the ring-shaped substance to deteriorate, because the etching operation is carried out using chemicals.

Further, in the conventional PTC heating device, the cylindrical portion 52 of the casing 50 and the cylindrical heat-radiating member 90 inserted through the longitudinal bore 52a of the cylindrical portion 52 extend in a direction at right angles to horizontal surfaces of the electrodes 80a and 80b of the PTC thermistor 80, so that heat generated at the electrodes 80a and 80b of the PTC thermistor 80, when the PTC heating device 500 is in use, will follow several paths to be transmitted to the heat-radiating member 90 serving as means for heating liquid insecticide having been sucked up the wick 46. More particularly, in the conventional PTC heating device, the horizontal surfaces of the electrodes 80a and 80b of the PTC thermistor 80 are out of contact with the cylindrical portion 52 and are in contact with the cover plate 100 and a bottom portion of the casing 50 through the upper electrode plate 70 and the lower electrode plate 60, respectively, so that heat generated at the electrodes 80a and 80b of the PTC thermistor 80, when the PTC heating device 500 is in use, will be transmitted through the upper electrode plate 70 and the lower electrode plate 60 to the cover plate 100 and the bottom portion of the casing 50, and then conducted to the heat-radiating member 90 through the cylindrical portion 52, thereby introducing a delay in transmitting the heat to the heat-radiating member 90. Therefore, in the conventional PTC heating device, it will take long for the heat-radiating member 90 to be heated to a temperature sufficient to vaporize liquid insecticide.

Also, a cylindrical constant temperature heating device which is similar to the above-described conventional PTC heating device and adapted to be used as a heater for preventing the freezing of a water-supply pipe or the like is found in Japanese Laid-Open Patent Publication No. 35490/1985. FIGS. 3 and 4 shows the constant temperature heating device. In FIGS. 3 and 4, components which are identical to those shown in FIG. 2 are identified by the same designators and the description of them will not be repeated. A reference numeral 300 designates a lead wire which is connected to the upper electrode 80a of the PTC thermistor 80 by solder or conductive adhesives 302, and a reference numeral 400 designates a lead wire which is connected to the lower electrode 80b of the PTC thermistor 80 by solder or conductive adhesives 402. This constant temperature heating device also has the above-described problems.

SUMMARY OF THE INVENTION

The present invention has been made with a view to overcoming the foregoing problems of the prior art device.

It is therefore an object of the present invention to provide a PTC heating device which is capable of efficiently heating liquid material to vaporize it.

It is another object of the present invention to provide a PTC heating device which is capable of immediately heating a heat-radiating member serving as means for heating a wick to a temperature sufficient to vaporize liquid material.

It is still another object of the present invention to provide a PTC heating device as stated above, which is simple and can be formed easily.

Generally speaking, in accordance with the present invention, a PTC heating device adapted to be incorporated in an electric vaporizer for heating liquid medicine such as liquid insecticide, aromatic liquid or the like, to vaporize it, the electric vaporizer including storage means for containing liquid medicine therein and absorber means for sucking up the liquid medicine from the storage means therethrough, the abosorber means consisting of an enlogated body which is immersed in the liquid medicine in the storage means, one end portion of which enlogated body projects from the storage means is provided which comprises at least one substantially plate-like PTC thermistor having a first electrode and a second electrode on its one and the other surface, respectively; first and second electrode members between which the at least one PTC thermistor is interposed, the first electrode member being in contact with the first electrode of the at least one PTC thermistor and the second electrode member being in contact with the second electrode of the at least one PTC thermistor; a casing of heat-resistant insulating material having a recess formed therein, within which recess, the at least one PTC thermistor and the first and second electrode members are received; a heat-conducting member being made of electrically insulating material which has good thermal conductivity and being mounted with respect to the casing to be in contact with the first electrode member; and a heat-radiating member having means for receiving the one end portion of the absorber means and being mounted with respect to the casing to be in contact with the first electrode member through the heat-conducting member; wherein heat generated at the at least one PTC thermistor in use is conducted to the heat-radiating memeber through the heat-conducting member, so that liquid medicine having been sucked up by means of the absorber means is heated due to the heat having been conducted to the heat-radiaiting member, to vaporize.

In a preferred embodiment of the present invention, the number of the PTC thermistors is at least two; the heat-conducting member comprises a body which is formed integrally with the casing in a manner to vertically protrude toward an opened side of the casing from a bottom of the recess of the casing and has a vertical through-hole provided therein for receiving the heat-radiating member and substantially planar surfaces which are formed on its side wall surrounding to through-hole; the heat-radiating member comprises a substantially cylindrical body having a longitudinal bore constituting the means for receiving the one end portion of the absorber means and inserted through the through-hole of the heat-conducting member of the casing, so that the heat-radiating member is in contact with an inner surface of the through-hole of the heat-conducing member; the first electrode member comprises substantially planar contact sections in contact with respective ones of the planar surfaces of the heat-conducting member; the at least two PTC thermistors are located on respective ones of the planar contact sections of the first electrode member in a manner such that the first electrode surfaces thereof are contacted with the respective ones of the planar contact sections of the first electrode member; and the second electrode member comprises contact sections in engagement with the second electrodes of the at least two PTC thermistors on the planar contact sections of the first electrode member to apply the first electrode surfaces of the at least two PTC thermistors onto the respective ones of the planar surfaces of the heat-conducting member through the planar contact sections of the first electrode member.

In a preferred embodiment of the present invention, the number of PTC thermistors is one; the first electrode member comprises a substantially planar contact section in contact with the first electrode of the PTC thermistor; the second electrode member comprises a contact section in engagement with the second electrode of the PTC thermistor; and the PTC thermistor and the first and second electrode members are assembled in the recess of the casing in superposed relation; the heat-conducting member is formed into a substantially plate-shape and arranged on the opened side of the casing while being located on the planar contact section of the first electrode member; and the heat-radiating member comprises a substantially U-shape body which has a substantially U-shape opening constituting the means for receiving the one end portion of the absorber means; and a pair of engaging arms which extend from both sides of the U-shape body in the opposite direction to the U-shape opening; and is arranged in contact on the heat-conducting member in a manner to hold both sides of the casing through the engaging arms.

In a preferred embodiment of the present invention, the PTC heating device further includes a cover plate formed into a substantially U-shape; and the casing is formed into a substantially U-shape and the recess of the casing has a substantially U-shape in the same posture as the casing, an U-shape opening side portion of which casing constitutes said heat-conducting member the first electrode member comprises a substantially U-shape body having a substantially planar contact section at each of its sides, and is received in the recess of the casing in a manner such that the planar contact section thereof are respectively engaged with both side regions of a wall surrounding said U-shape opening of the casing; the number of the PTC thermistors are two, the PTC thermistors being respectively located on the planar contact sections of the first electrode member in a manner such that the first electrodes thereof are respectively contacted with the planar contact sections of the first electrode member; the second electrode member comprises a substantially U-shaped body having a contact section at each of its sides, and is received in the recess of the casing in a manner such that the planar contact sections thereof are respectively engaged with the second electrodes of the PTC thermistors on the planar contact sections of the first electrode member; the U-shaped cover plate is arrange, in the same posture of said casing, on the casing have said electrode members and the PTC thermistors received therein to close the recess of the casing;

said heat-radiating member comprises a body of a substantially inverted symbol-of-ohm shape which has a substantially U-shape opening constituting means for receiving the one end portion of the absorber means, and a socket portion formed along the body thereof; and an assembly of the casing having the electrode members and the PTC thermistors received therein and the cover plate is fitted in the socket portion of the heat-radiating member at its opened side portion while receiving a central protruding portion of the heat-radiating member in its opening.

BRIEF DESCRIPTION OF THE DRAWINGS

These and other objects and many of the attendant advantages of the present invention will be readily appreciated as the same becomes better understood by reference to the following detailed description when considered in connection with the accompanying drawings, in which like reference numerals designate the same parts through the Figures and wherein;

FIG. 1 schematically shows a vertical sectional view of an electric mosquito destroyer;

FIG. 3 is an exploded perspective view showing another conventional constant temperature heating device;

FIG. 7 is an enlarged vertical sectional view of the PTC heating device according to the first embodiment, take on a plane indicated at FIG. 6 by a line A—A;

FIG. 8 is an enlarged plan view of the PTC heating device according to the first embodiment, wherein a cover plate and a mounting plate are removed from a casing for clarity of illustration;

FIG. 9 is an exploded perspective view showing a modification of the first embodiment; FIG. 10 is a schematic perspective view of the modification into which parts thereof shown in FIG. 9 are assembled;

FIG. 13 is a sectional view showing another modification of the PTC heating device of the first embodiment;

FIG. 15 is a schematic perspective view of the PTC heating device shown in FIG. 14 into which parts thereof shown in FIG. 14 are assembled;

FIG. 20 is an enlarged segmentary sectional view of assistance in explaining projecting of a lead-out terminal of the electrode member of FIG. 19 outwardly of a casing:

FIG. 21 is an enlarged perspective view showing a first electrode member;

FIG. 22 schematically shows a vertical sectional view of an electric mosquito destroyer having the PTC heating device of FIG. 15 incorporated therein;

DETAILED DESCRIPTION OF THE PREFERRED EMBODIMENTS

Figure 5:
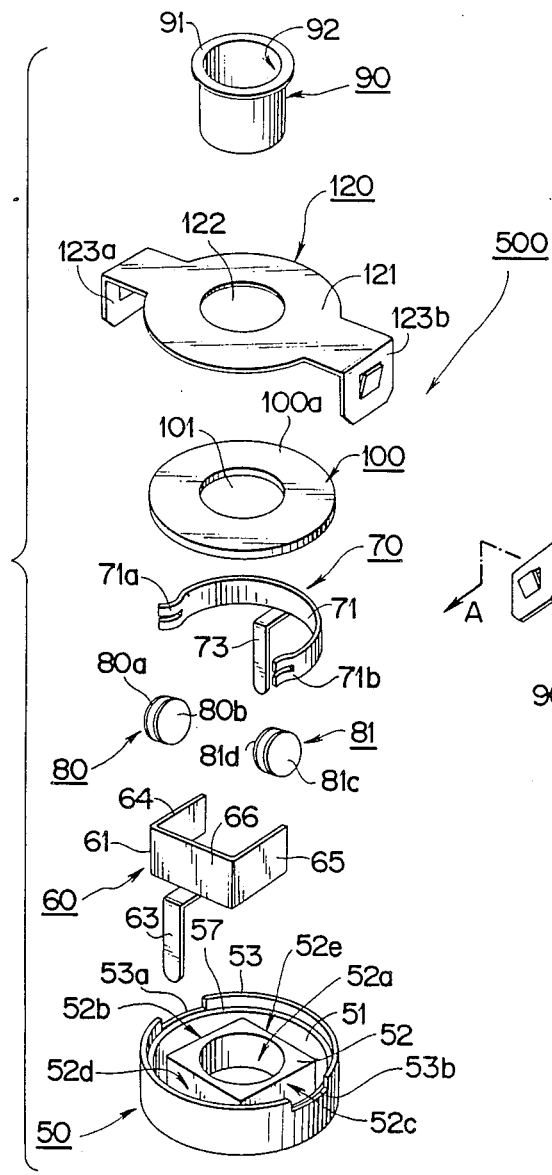
FIG. 5 is an exploded perspective view showing a PTC heating device according to a first embodiment of this invention.
Figure 6:
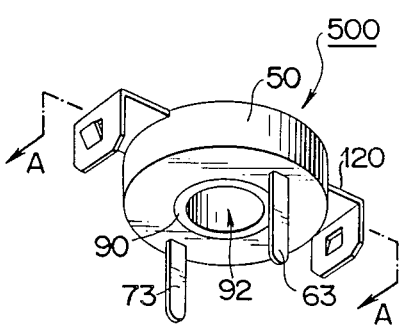
FIG. 6 is a schematic perspective view of the PTC heating device according to the first embodiment of this invention, into which parts thereof shown in FIG. 5 are assembled.
Figure 11:
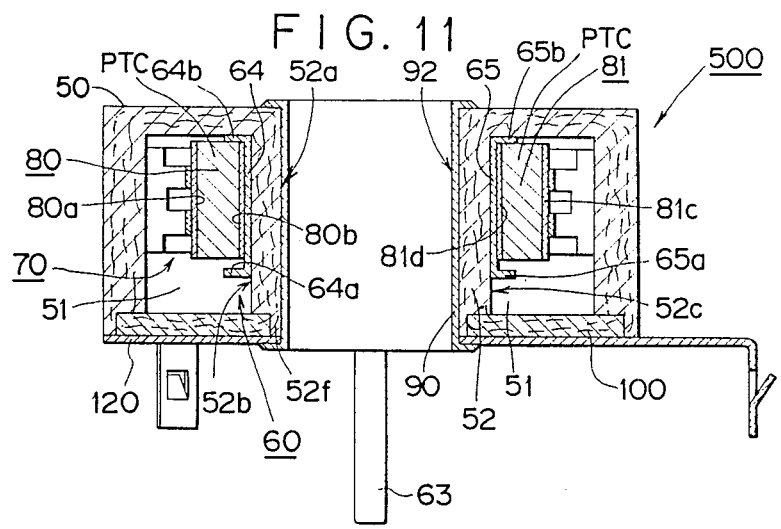
FIG. 11 is an enlarged vertical sectional view of the PTC heating device shown in FIG. 10, taken on a plane indicated at FIG. 10 by a line B—B.

Referring to FIGS. 5 and 8, a PTC heating device 500 according to a first embodiment of this invention comprises a casing 50, first and second electrode members 60 and 70 which are received in the casing 50, a pair of substantially disc-shaped PTC thermistors 80 and 81 which are interposed between the first and second electrode members 60 and 70 and received in the casing 50, a heat-radiating member 90 of a substantially cylindrical shape which is made of metal such as aluminum or the like, a cover plate 100 mounted with respect to the casing 50, and a mounting plate 120 arranged on the cover plate 100 and for mounting the PTC heating device 500 with respect to an armoring case of an electric mosqito destroyer therethrough.

The casing 50 is made of a heat-resistant electrically insulating material which has good thermal conductivity, for example, alumina porcelain or the like, and comprises a body having a recess 51 to form a hollow for receiving the first and second electrode members 60 and 70 and the PTC thermistors 80 and 81 therein, and a substantially box-like heat-conducting portion 52 which is formed integrally with the casing body so as to protrude upwardly from a substantially central portion of the bottom of the recess 51. The heat-conducting portion 52 is slightly less in height than a circular side wall 53 of the casing body surrounding the recess 51. The casing 50 further has a through-hole 52a of a substantially cylinder-shape which extends vertically from the outer bottom surface of the recess 51 to the upper surface of the heat-conducting portion 52, a circular step portion 57 which is integrally formed along the inner surface of the circular side wall 53 and lies in the same plane as the upper surface of the heat-conducting portion 52, and two notches 53a and 53b which are formed at upper positions of the side wall 53 and positioned opposite each other.

The first electrode member 60 is made of an elastic and conductive material such as stainless steel or the like and comprises a substantially U-shaped body 61 consisting of planar side plates 64 and 65 and an intermediate plate 66 which interconnects the planar side plates 64 and 65, and a substantially inverted L-shape lead-out terminal 63 which depends from a lower edge portion of the intermediate plate 66. The first electrode member 60 is received in the recess 51 of the casing 50 in a manner such that the planar side plates 64 and 65 of the U-shaped body 61 thereof come into contact with planar outer surfaces of sidewalls of the box-like heat-conducting portion 52 which are opposite to each other, respectively. In the example being illustrated, the first electrode member 60 is received in the recess of the casing 50 in a manner such that the planar side plates 64 and 65 thereof come into contact with planar sidewalls 52b and 52c of the heat-conducting portion 52 of the casing 50, respectively, but the first electrode member 60 may be received in the recess 51 of the casing 50 in a manner such that the planar side plates 64 and 65 thereof come into contact with planar sidewalls 52d and 52e of the heat-conducting portion 52 of the casing 50, respectively. As shown in FIG. 8, the lead-out terminal 63 of the first electrode member 60 is projected outwardly of the casing 50 via a through-hole 50a which is formed at the bottom of the casing 50.

The second electrode member 70 is made of the same material as the first electrode member 60 and comprises a strip-like body 71 which is curved into a substantially C-shape, and a substantially inverted L-shape lead-out terminal 73 which depends from a generally intermediate portion of the body 71. Both end portions 71a and 71b of the body 71 are each forked into two branches and curved inwardly of the C-shaped body 71, thereby exhibiting elasticity. The second electrode member 70 is received in the recess 51 of the casing 50 in a manner such that the C-shaped body 71 thereof is elastically applied onto a region of a side surface of the circular step portion 57 of the casing 50 which faces toward an opened side of the U-shaped body 61 of the first electrode member 60 received in the recess 51 in the manner described above, and in a manner such that the both end portions 71a and 71b of the C-shaped body 71 are located opposite to the side plates 64 and 65 of the first electrode member 60, respectively. The lead-out terminal 73 of the second electrode member 70 is projected outwardly of the casing 50 via a through-hole 50b which is formed at the bottom of the casing 50 as shown in FIG. 8.

The PTC thermistors 80 and 81 are each formed into a disc-like shape as described above. The PTC thermistor 80 has a first electrode 80a and a second electrode 80b on its one flat surface and the other flat surface, respectively. This PTC thermistor 80 is interposed between the side plate 64 of the first electrode member 60 and the inwardly curved end portion 71a of the C-shaped body 71 of the second electrode member 70 in a manner such that the first electrode 80a and second electrode 80b thereof come into contact with the inwardly curved end portion 71a of the second electrode member 70 and the planar side plate 64 of the first electrode member 60, respectively, so that the PTC thermistor 80 is in close contact with the planar sidewall 52b of the heat-conducting portion 52 of the casing 50 through the side plate 64 of the first electrode member 60 due to an elastic force of the inwardly curved end portion 71a of the C-shaped body 71 of the second electrode member 70. Same as the PTC thermistor 80, the PTC thermistor 81 has a first electrode 81c and a second electrode 81b on its one flat surface and the other flat surface, respectively. This PTC thermistor 81 is interposed between the side plate 65 of the first electrode member 60 and the inwardly curved end portion 71b of the C-shaped body 71 of the second electrode member 70 in a manner such that the first electrode 81c and second electrode 81d thereof come into contact with the inwardly curved end portion 71b of the second electrode member 70 and the planar side plate 65 of the first electrode member 60, respectively, so that the PTC thermistor 81 is in close contact with the flat sidewall 52c of the heat-conducting portion 52 of the casing 50 through the side plate 65 of the first electrode member 60 due to an elastic force of the inwardly curved end portion 71b of the C-shaped body of the second electrode member 70.

The cover plate 100 is made of a heat-resistant plastic material or a porcelain material and has a substantially ring-shaped body 100a, a diameter of which ring-shaped body 100a is slightly less than that of the circular side wall 53 of the casing 50 and a diameter of a through-hole 101 of which ring-shaped body 100a is the same as that of the through-hole 52a of the heat-conducting portion 52 of the casing 50. This cover plate 100 is fitted into the casing 50 in a manner to be supported on the step portion 57 and upper surface of the heat-conducting portion 52 of the casing 50 and in a manner such that the through-hole 101 thereof is aligned with the through-hole 52a of the heat-conducting portion 52 of the casing 50, whereby the cover plate 100 blocks up the recess 51 of the casing 50.

The mounting plate 120 has a substantially ring-shaped body 121, a diameter of which ring-shaped body 121 is the same as that of the circular side wall 53 of the casing 50 and a diameter of a through-hole 122 of which ring-shaped body 121 is the same as that of the through-hole 52a of the heat-conducting portion 52 of the casing 50. Also, the mounting plate 120 includes two substantially inverted L-shape arms 123a and 123b which extend radially from the ring-shaped body 121 and positioned about 180° around the ring-shaped body 121 from each other. This mounting plate 120 is arranged on the cover plate 100 in a manner such that horizontal portions of the arms 123a and 123b thereof are engaged with the notches 53a and 53b of the casing 50, respectively, and in a manner such that the through-hole 122 thereof is aligned with the through-hole 52a of the heat-conducting portion 52 of the casing 50. In the example being illustrated, the mounting plate 120 is provided with two inverted L-shape arms but may be provided with three inverted L-shape arms.

The cylindrical heat-radiating member 90 is more in length than a height of the side wall 53 of the casing 50. A diameter of the heat-radiating member 90 is slightly less than those of the through-hole 52a of the heat condcuting portion 52 of the casing 50, of the through-hole 101 of the cover plate 100, and of the through-hole 122 of the mounting plate 120. The cylindrical heat-radiating member 90 is provided at its one end with a flange 91 and is mounted with respect to the casing 50 in a manner such that the other end thereof is inserted through the through-hole 122 of the mounting plate 120, the through-hole 101 of the cover plate 100, and the through-hole 52a of the heat-conducting portion 52 of the casing 50 to be riveted over the outer bottom surface of the recess 51 of the casing 50, to thereby securely hold the cover plate 100 and the mounting plate 120 with respect to the casing 50 through the heat-radiating member 90.

Incidentally, a contact surface between the cover plate 100 and the step portion 57 of the casing 50, the notches 53a and 53b, and the through-holes 50a and 50b for the lead-out terminals 63 and 73 of the first and second electrode members 60 and 70 are sealed with sealing compounds or adhesives, thereby preventing liquid material and/or vaporized material from entering the recess 51 of the casing 50.

Figure 12:
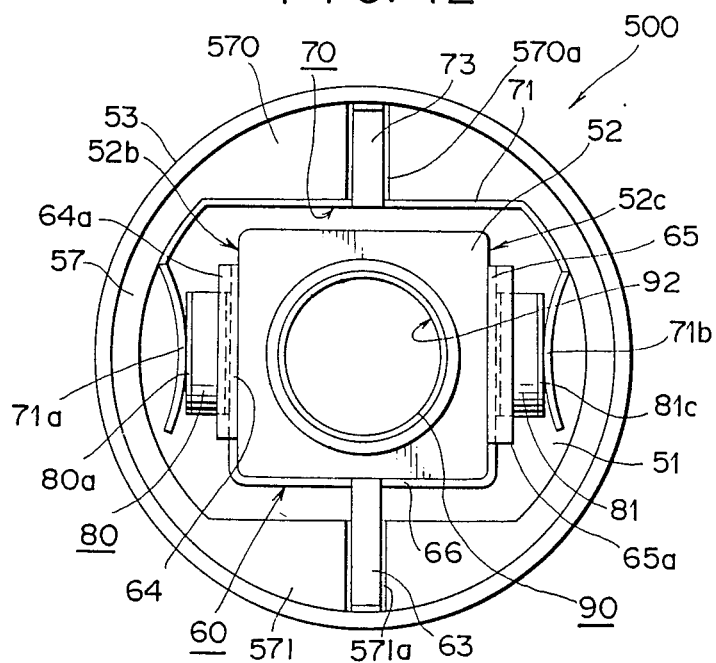
FIG. 12 is an enlarged bottom view of the PTC heating device shown in FIG. 10, wherein a cover plate and a mounting plate are removed from a casing for clarity of illustration.

A modification of the first embodiment is shown in FIGS. 9 to 12. In the modification of FIGS. 9 and 12, parts which are identical to those shown in FIGS. 5 to 8 are identified by the same designators and the description of them will not be repeated. Incidentally, in FIG. 9, the respective parts of this modification are shown in a state of being turned upside down for clarity of illustration. Practically, this PTC heating device is mounted, in a posture shown in FIG. 10, with respect to an electric mosquito destroyer.

Referring now to FIGS. 9 to 12, the side plate 64 of the first electrode member 60 is provided at upper and lower edge portions thereof with bent portions 64a and 64b which are bent at right angles to the flat side plate 64 and extend toward the PTC thermistor 80 on the side plate 64. Like the side plate 64, the side plate 65 of the first electrode member 60 is provided at upper and lower edge portions thereof with bent portions 65a and 65b which are bent at right angles to the flat side plate 65 and extend toward the PTC thermistor 81 on the side plate 65. The first electrode member 60 is generally made by stamping a sheet of stainless steel or the like, resulting in producing burrs on the side plates 64 and 65. In the case where burrs actually exist on the side plates 64 and 65 of the first electrode member 60, when the PTC thermistors 80 and 81 are respectively arranged on the side plates 64 ad 65 of the first electrode member 60 for assembly, they are located on the side plates 64 and 65 in a state of being on the burrs of the side plates 64 and 65, so that the close contact of the respective PTC thermistors 80 and 81 with the side plates 64 and 65 of the first electrode member 60 is prevented, thereby preventing efficient and rapid transmitting of heat from the PTC thermistors 80 and 81 to the heat-radiating member 90. In the modification of FIGS. 9 to 12, such burrs are absorbed by the bent portions 64a and 64b, and 65a and 65b, thereby providing the close contact of the PTC thermistors 80 and 81 with the side plates 64 and 65 of the first electrode member 60.

Further, in the modification of FIGS. 9 to 12, as shown in FIG. 9, the lead-out terminal 63 of the first electrode member 60 extends upwardly from the upper edge portion of the intermediate plate 66 of the first electrode member 60. Like the lead-out terminal 63 of the first electrode member 60, the lead-out terminal 73 of the second electrode member 70 extends upwardly from the upper edge portion of the body 71 of the second electrode member 70. Also, the second electrode member body 71 is formed into a substantially U-shape and received in the recess 51 in a manner such that an opened side thereof faces toward the opened side of the first electrode member body 61. Further, in the modification of FIGS. 9 to 12, as shown in FIG. 9, the box-like heat-conducting portion 52 is provided with a protruding portion 52f of a circular shape which is formed integrally with the heat-conducting portion 52 in a manner to protrude outwardly from the through-hole 52a of the heat-conducting portion 52. Furthermore, the step portion 57 of the casing 50 includes two inward projecting portions 570 and 571 which are respectively formed at positions of the step portion 57 where are opposite to each other. The inward projecting portions 570 and 571 are provided with grooves 570a and 571a, respectively. A horizontal portion of the L-shape lead-out terminal 63 of the first electrode member 60 is engaged with the groove 571a of the projecting portion 571, while a horizontal portion of the L-shape lead-out terminal 73 of the second electrode member 70 is engaged with the groove 570a of the projecting portion 570. Further, in the modification of FIGS. 9 to 12, the ring-shaped cover plate 100 is formed with two notches 100b and 100c which are positioned approximately 180° around the cover plate 100 from each other, and the mounting plate 120 is provided with three L-shape arms 123a, 123b and 123c which extend radially from the ring-shaped body 121 and are positioned approximately 120° around the ring-shaped body 121 from one another. A diameter of the through-hole 101 of the cover plate 100 is slightly more than that of the protruding portion 52f of the heat-conducting portion 52. The cover plate 100 is supported on the step portion 57 and the upper surface of the box-like heat-conducting portion 52 in a manner to be fitted on the protruding portion 52f through the through-hole 101 thereof and in a manner such that the notches 100b and 100c thereof are aligned with grooves 570a and 571a of the step portion 57, respectively. The vertical portions of the L-shape lead-out terminals 63 and 73 are led outwardly through the notches 100b and 100c of the cover plate 100, respectively. Generally speaking, in this type of PTC heating device, the casing 50 should be completely sealed in order to prevent liquid material and/or vaporized insecticide from entering the casing 50 to deteriorate the PTC thermistors 80 and 81 and the electrode members 60 and 70 which are received in the recess 51 of the casing 50. For this purpose, a contact surface between the cover plate 100 and the step portion 57 of the casing 50, the notch 100b of the cover plate 100 through which the vertical portion of the L-shape lead-out terminal 72 is led out from the casing 50, and the notch 100c of the cover plate 100 through which the vertical portion of the L-shape lead-out terminal 63 is led out from the casing 50 are sealed with, e.g., sealing compounds or adhesives. In the modification of FIGS. 9 to 12, such portions which should be sealed are located on the same side, namely, the opened side of the casing 50, so that the sealing operation is easily carried out.

The remaining parts of the modification of FIGS. 9 to 12 are constructed and arranged in substantially the same manner as those shown in FIGS. 5 to 8.

Referring to FIG. 13, the heat-conducting portion 52 is formed independently of the casing body 50. In the PTC heating device 500 of FIG. 13, where the heat-conducting portion 52 is made of a heat-resistant electrically insulating material which is superior in its thermal conductivity to the casing 50, the heat conducting property can be improved. Also, in the case where the heat-conducting portion 52 is made of a thermal insulating material, heat generated at the PTC thermistors 80 and 81 is prevented from escaping.

Figure 14:
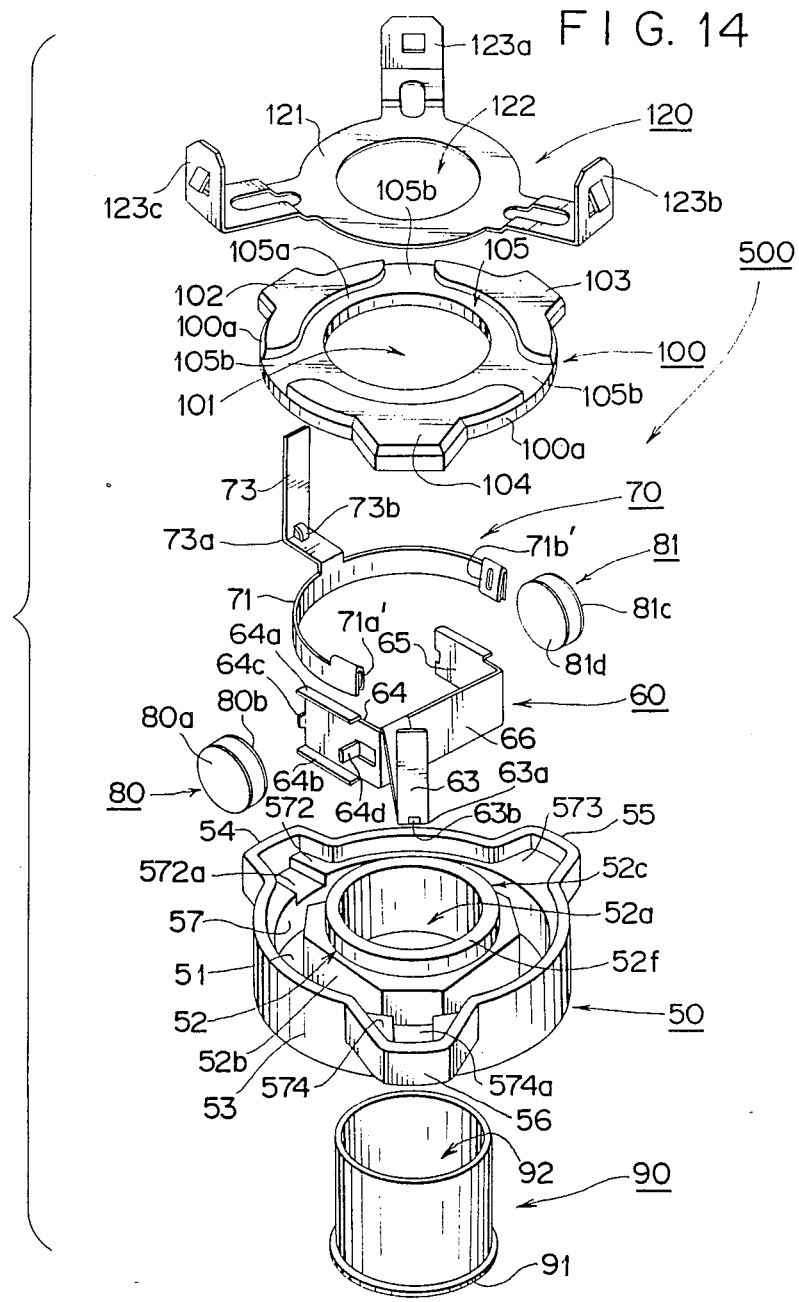
FIG. 14 is an exploded perspective view showing still another modification of the first embodiment.
Figure 18:
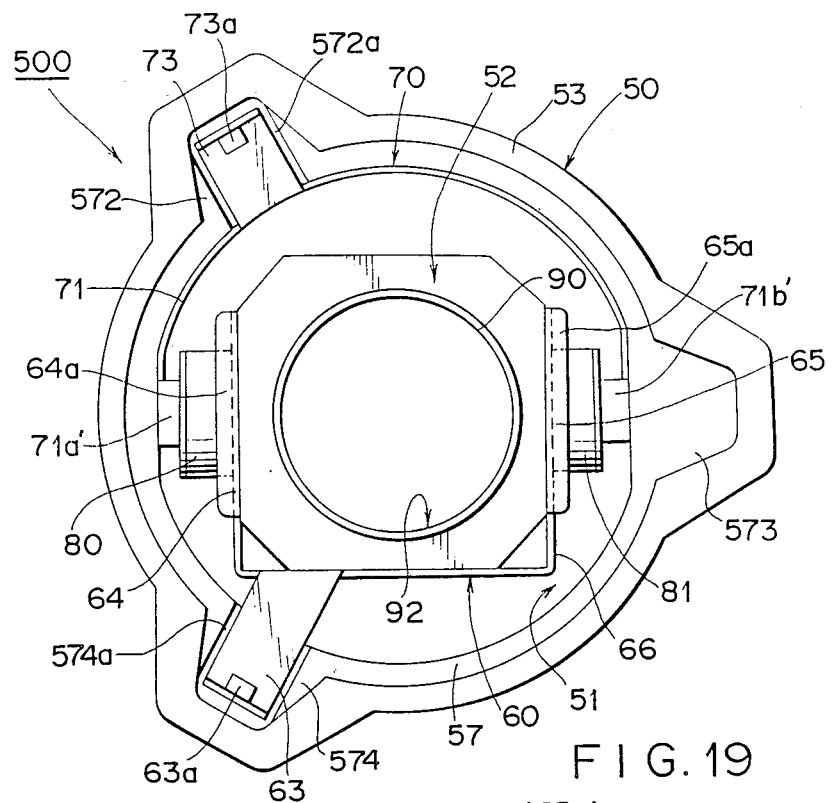
FIG. 18 is an enlarged bottom view of the PTC heating device of FIG. 15, wherein a cover plate and a mounting plate are removed from a casing for clarity of illustration.

FIGS. 14 and 18 show another modification of the first embodiment. In this modification, parts which are similar to those shown in FIGS. 5 to 13 are designated with like reference numerals and the description of them will not be repeated. Incidentally, in FIG. 14, the respective parts of this modification are shown in a state of being turned upside down for clarity of illustration. Practically, this PTC heating device is mounted, in a posture shown in FIG. 15, with respect to an electric mosquito destroyer. Referring to FIGS. 14 to 18, a PTC heating device 500 of this modification is generally similar to that of FIGS. 5 to 13 except that the cover plate 100 is adapted to be locked with respect to the casing 50 and the mounting plate 120 is also adapted to be locked with respect to the cover plate 100. More particularly, in the modification of FIGS. 14 to 18, like the heat-conducting portion of FIG. 9, the heat-conducting portion 52 includes the protruding portion 52f but has eight planar surfaces on the surrounding sidewall thereof, unlike the heat-conducting portion 52 of FIG. 9. The PTC thermistors 80 and 81 are respectively in contact with two of these planar surfaces of the heat-conducting portion 52, for example, planar surfaces 52b and 52c which are opposite to each other, through the side plates 64 and 65 of the first electrode member 60. Further, the casing 50 is provided with three protruding portions 54, 55 and 56 which project radially from the circular side wall 53 at about 120° intervals around the circular side wall 53. Correspondingly, the step portion 57 extend outwardly along the sidewall 53 at positions where the protruding portions 54, 55 and 56 are located, to form three concavities 572, 573 and 574 by the protruding portions of the side wall 53 and the outwardly extending portions of the step portion 57, two of which 572, 573 and 574, for example, the concavities 572 and 574 are formed with grooves 572a and 574a, respectively. The horizontal portion of the L-shaped terminal 73 of the second electrode member 70 is engaged with the groove 572a, while the horizontal portion of the L-shaped terminal 63 of the first electrode member 60 is engaged with the groove 574a.

Figure 19:
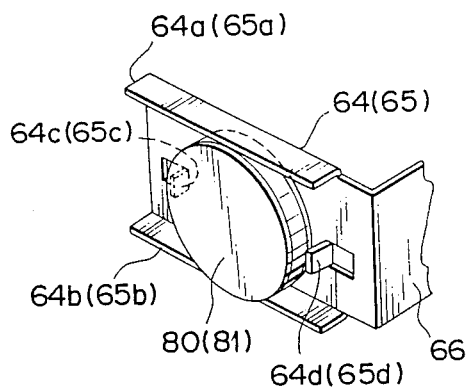
FIG. 19 is an enlarged segmentary perspective view of an electrode member which is incorporated in the PTC heating device of FIG. 15.

The first electrode member 60 of this modification is generally similar to that of FIG. 9 except that the planar side plate 64 includes tongue-like pieces 64c and 64d which extend toward the PTC thermistor 80 on the side plate 64 at right angles to the flat side plate 64 and are located at right and left sides of the side plate 64, respectively, and the planar side plate 65 includes tongue-like pieces 65c and 65d (see FIG. 19) which extend toward the PTC thermistor 81 on the side plate 65 at right angles to the planar side plate 65 and are located at right and left sides of the side plate 65, respectively. In this modification, the PTC thermistor 80 is located on the side plate 64 of the first electrode member 60 in a manner to be surrounded by the bent portions 64a and 64b and the tongue-like pieces 64c and 64d, thereby preventing the PTC thermistor 80 from moving on the side plate 64. Likewise, the PTC thermistor 81 is located on the side plate 65 of the first electrode member 60 in a manner to be surrounded by the bent portions 65a and 65d and the tongue-like pieces 65c and 65d, thereby preventing the PTC thermistor 81 from moving on the side plate 65. Further, the L-shaped terminal 63 of the first electrode member 60 is provided at a corner portion 63a thereof with a substantially quadrant-shaped rib 63b which is formed by cutting out a part of the corner portion 63a and curving the same inwardly of the corner portion 63a.

The second electrode member 70 is generally similar to that of FIG. 5 except that the C-shaped body 71 is provided at the both end portions 71a and 71b thereof with inward bent pieces 71a' and 71b', and the L-shaped terminal 73 extends upwardly from the C-shaped body 71 and is provided at a corner portion 73a thereof with a substantially quadrant-shaped rib 73b which is formed cutting out a part of the corner portion 73a and curving the same inwardly of the corner portion 73a.

As described above, the L-shaped terminals 63 and 73 are provided at their corner portions 63a and 73a with the ribs 63b and 73b, respectively, thereby providing mechanical strength for the terminals 63 and 73.

Figure 16:
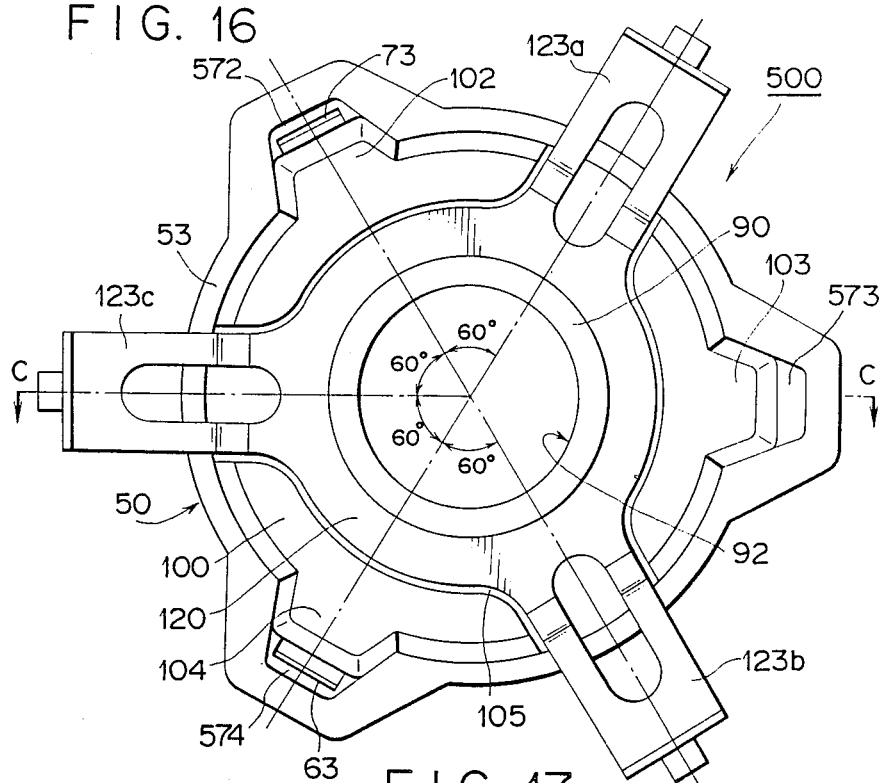
FIG. 16 is an enlarged bottom view of the PTC heating device shown in FIG. 15.
Figure 17:
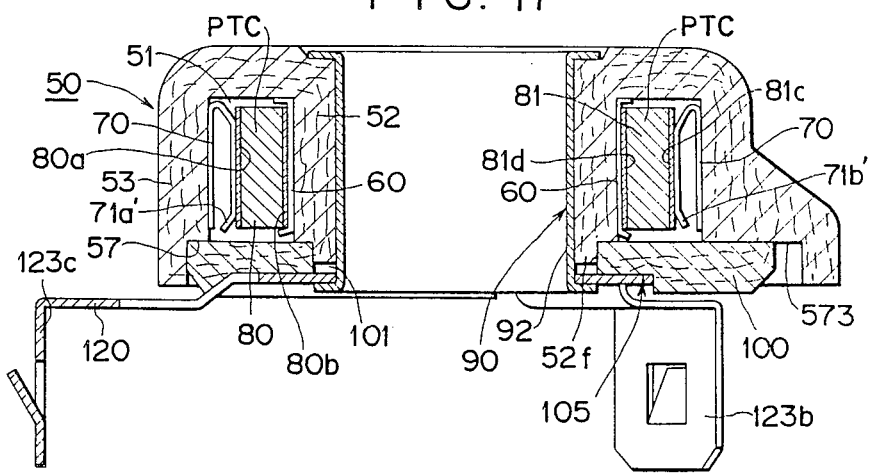
FIG. 17 is an enlarged vertical sectional view of the PTC heating device shown in FIG. 15, taken on a plane indicated at FIG. 16 by a line C—C.

A cover plate 100 of the modification shown in FIG. 14 comprises a ring-shaped body 100a and three protruding portions 102, 103 and 104 which extend radially from the periphery of the body 100a and are positioned about 120° intervals around the ring-shaped body 100a. The cover plate 100 is arranged on the opened side of the casing 50 in a manner to be supported on the upper surface of the heat-conducting portion 52 and the step portion 57, and in a manner such that the protruding portions 102, 103 and 104 of the cover plate 100 are engaged with three concavities of the casing 50, respectively, thereby prevent the cover plate 100 from being rotated on the heat-conducting portion 52 and the step portion 57. In the example being illustrated, the protruding portions 102, 103 and 104 of the cover plate 100 are engaged with the concavities 572, 573 and 574, respectively. Further, each of the protruding portions 102, 103 and 104 of the cover plate 100 is short enough to allow a clearance to be provided between its tip end and the tip end of corresponding protruding portion of the side wall 53, through which clearance the vertical portion of each of the L-shaped terminals 63 and 73 extends out of the casing 50. Naturally, after assembly of the PTC heating device, the clearance is sealed with sealing compounds or adhesives as will later be described. The cover plate 100 is provided with a depression 105 formed in the body 100a, which depression 105 includes central portion 105a around the through-hole 101 of the cover plate 100 and three portions 105b which extend radially from the central portion 105a to the periphery of the body 100a and are respectively located at a substantially middle position between a position where the protruding portion 102 is located and a position where the protruding portion 103 is located, at a substantially middle position between a position where the protruding portion 103 is located and a position where the protruding portion 104 is located, and at a substantially middle position between a position where the protruding portion 104 is located and a position where the protruding portion 102 is located. As shown in FIG. 20, the cover plate 100 is mounted with respect to the casing 50 by bonding the cover plate 100 to the step portion of the casing 50 with adhesives X. Incidentally, when adhesive is filled in the concavity of the side wall 53 for bonding of the cover plate 100 and the step portion of the casing 50, the adhesive X becomes spreaded in the concavity of the side wall 53 through a space between the corner portion of the L-shaped terminal and the rib, thereby facillitating the bonding operation of the cover plate 100 and the casing 50. On the cover plate 100 mounted with respect to the casing 50 in the manner described above, the mounting plate 120 which is similar to that shown in FIG. 9 is arranged. More particularly, the mounting plate body 121 is slightly protruded toward the cover plate 100 and the mounting plate 120 is assembled with respect to the cover plate 100 in a manner such that the ring-shaped body 121 thereof is engaged with the central position 105a of the depression 105 of the cover plate 100 and the horizontal portions of the L-shaped arms 123a to 123c thereof are partially engaged with the radially extending portions 103b of the depression 105 of the cover plate 100, respectively, thereby preventing the mounting plate 120 from being rotated on the cover plate 100. As described above, the terminal of each of the first and second electrode members 60 and 70 is led out of the casing 50 through the clearance between the radially protruding portion of the cover plate 100 and the concavity of the sidewall 53 of the casing 50, while each of the arms 123a to 123c of the mounting plate 120 is engaged with one of the radially extending portions 105b of the depression 105 which is located at the substantially middle position between the respective protruding portions of the cover plate 100, namely, the terminal of each of the electrode members 60, 70 and each of the arms 123a to 123c of the mounting plate 120 are spaced from each other at about 60° as shown in FIG. 16. Thus, adequate electrical insulation is provided between the terminals and the arms.

In the modification shown in FIG. 14, the terminals 63 and 73 of the electrode members 60 and 70 are led out of the casing 50 from the opened side of the casing 50 on which the cover plate 100 is arranged. However, it will be understood that the terminals 63 and 73 can be led out of the casing 50 through the bottom of the recess 51. Also, the mounting plate 120 may be arranged on the outer bottom surface of the recess 51 of the casing 50. In this case, depression (corresponding to the depression 105 of the cover plate 100) is formed on the outer bottom surface of the recess 51.

As shown in FIG. 21, the first electrode member 60 may be constructed in a manner such that each of the side plates 64 and 65 is connected to the intermediate plate 66 by two strips 67 and 68, one 67 of which strips is thinner than the other 68 and act as an excessive current fusion section. The thick strip 68 is provided for mechanical strength and adapted to be cut after incorporating of the first electrode member 60 within the recess 51 of the casing 50 as shown in FIG. 21.

FIG. 22 shows a vertical sectional view of an electric mosquito destroyer having the PTC heating device 500 of FIG. 15 incorporated therein.

Referring to FIG. 22, the electric mosquito destroyer comprises an upper case 40 having a through-hole 40a formed at its upper wall 40b, and a lower case 42 having a supporting section 48 for supporting the PTC heating device 500 therethrough and mounted in the interior of the lower case 42. In FIG. 22 reference numeral 44 designates a reservoir having liquid insecticide contained therein, and a reference numeral 46 designates a wick for sucking up liquid insecticide from the reservoir 44, which wick 46 has an elongated body made of fibrous material such as felt, or porous material. The elongated wick 46 is inserted into the reservoir 44 through a mouth of the reservoir 44 to be immersed in the liquid insecticide contained in the reservoir 44, an upper end portion of which elongated wick 46 projects from the mouth of the reservoir 44 to be inserted into the longitudinal bore 92 of the heat-radiating member 90 of the PTC heating device 500. The supporting section 48 includes a horizontal plate 48a having through-holes 48b. The PTC heating device 500 is located on the horizontal plate 48a of the supporting section 48 in a manner such that tip end portions of the arms 123a and 123c of the mounting plate 120 thereof are respectively inserted through the through-holes 48b of the horizontal plate 48a.

In the electric mosquito destroyer constructed as described above, when heat is generated at the PTC thermistors 80 and 81 of the PTC heating device 500 to be transmitted to the heat-radiating member 90, the upper end portion of the wick 46 having sucked up liquid insecticide from the reservoir 44 is heated due to the heat which has been conducted to the heat radiating member 90, resulting in the liquid insecticide vaporizing. Thus, the vaporized insecticide is diffused out of the electric mosquito destroyer through the through-hole 40a of the upper case 40.

Figure 2:
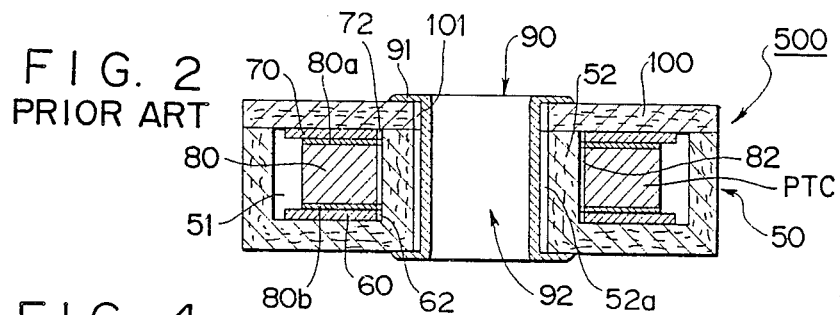
FIG. 2 is a vertical sectional view of one conventional PTC heating device.
Figure 4:
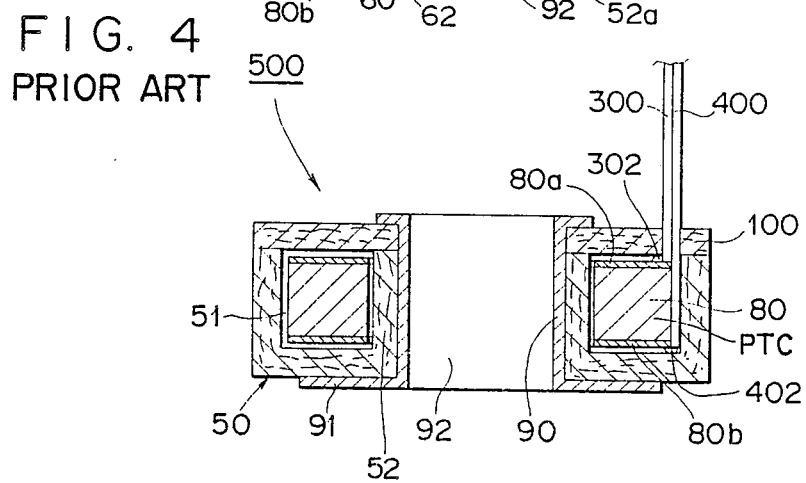
FIG. 4 is a vertical sectional view of the conventional constant temperature heating device into which parts thereof shown in FIG. 3 are assembled.

In the PTC heating device 500 of the first embodiment, the electrodes of the PTC thermistors 80 and 81 are in close contact with the flat surfaces of the side walls of the heat-conducting portion 52 of the casing 50 through the side plates 64 and 65 of the first electrode member 60, respectively, contrary to the prior art showing in FIGS. 2 and 4. Therefore, in the PTC heating device 500 of the first embodiment, when is generated at the electrodes of the PTC thermistors 80 and 81 in use of the PTC heating device 500, the heat is efficiently and rapidly transmitted to the heat-radiating member 90 through the heat-conducting portion 52 of the casing 50. Further, as will be appreciated from the description on the first embodiment, the temperature distribution on the inner surface of the heat-radiating member 90 is uniform, so that the wick 46 which is inserted into the longitudinal bore 92 of the heat-radiating member 90 at its upper end portion is heated at an uniform temperature, particularly, in the case where the PTC thermistors 80 and 81 are in close contact with the flat surfaces of sidewalls of the heat-conducting portion 52 of the casing 50 which are opposite to each other as the example being illustrated, the temperature distribution on the inner surface of the heat-radiating member 90 reaches more uniformity.

Figure 23:
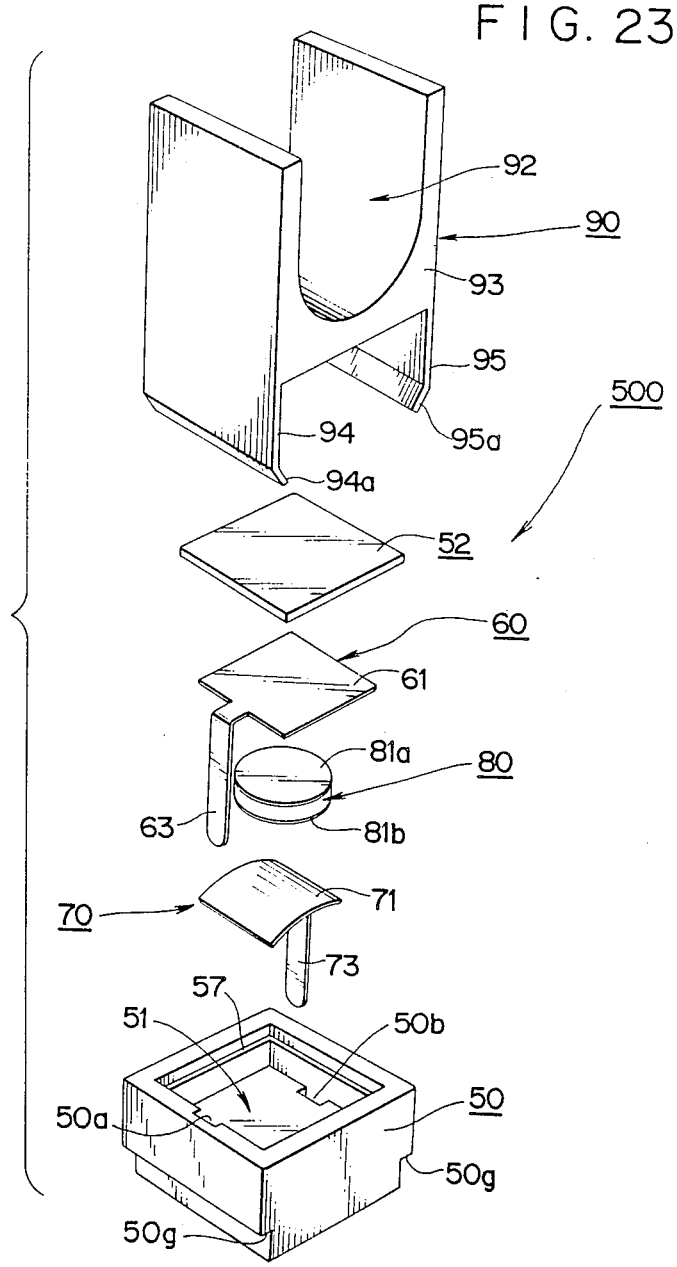
FIG. 23 is an exploded perspective view of a PTC heating device according to a second embodiment of this invention.
Figure 24:
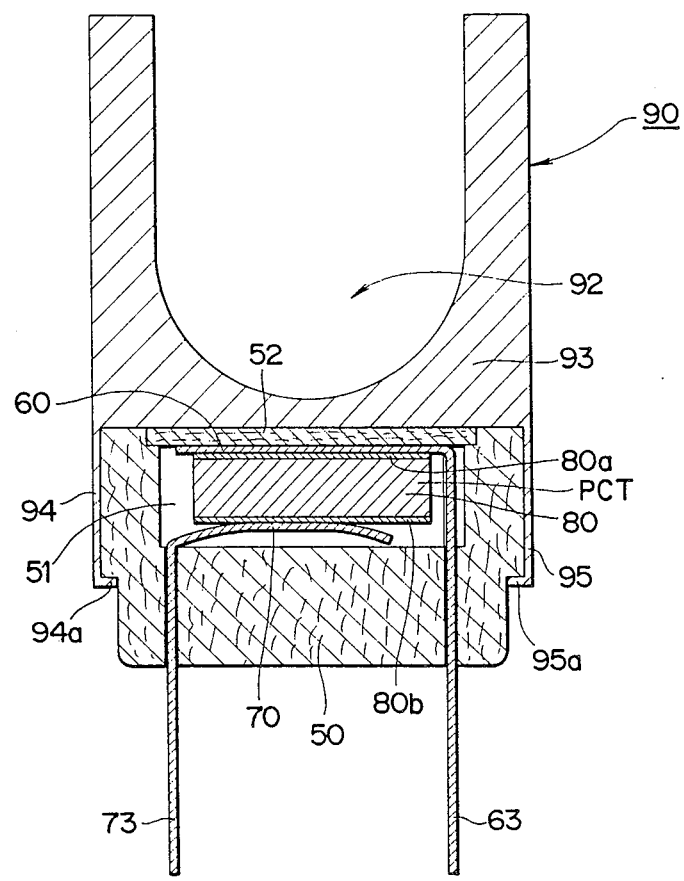
FIG. 24 is an enlarged sectional view showing the PTC heating device of FIG. 23, into which parts thereof shown in FIG. 23 are assembled.

Referring to FIGS 23 and 24, a PTC heating device 500 according to a second embodiment of this invention comprises a disc-like PTC thermistor 80 having a first electrode 80a and a second electrode 80b on its one and other surfaces, respectively; first and second electrode members 60 and 70 between which the PTC thermistor 80 is vertically interposed; a casing 50 having a recess 51 formed therein, within which recess 51, the PTC thermistor 80 and the first and second electrode members 60 and 70 are received; a heat-conducting plate 52 being formed of a heat-resistant electrically insulating material which has good thermal conductivity, for example, alumina porcelain or the like, and being positioned on the first electrode member 60; and a heat-radiating member 90 arranged on the heat-conducting plate 52 in a manner to cover the casing 50.

The casing 50 is made of a heat-resistant electrically insulating material, for example, heat-resistant plastic material or the like. The first electrode member 60 comprises a planar plate 61 and a substantially inverted L-shape lead-out terminal 63 depending from the planar plate 61. Likewise, the second electrode member 70 comprises a bowed plate 71 which is upwardly bowed to exhibit elasticity, and a substantially inverted L-shape lead-out terminal 73 depending from the bowed plate 71. The first and second electrode members 60 and 70 are each made from a sheet of stainless steel. As described above, the PTC thermistor 80 and the first and second electrode members 60 and 70 are assembled in the recess 51 of the casing 50 in superposed relation. When the electrode members 60 and 70 are received in the recess 51 of the casing 50 together with the PTC thermistor 80 for assembly, the terminal 63 of the first electrode member 60 is led out of the casing 50 via a groove 50a which is vertically formed in a side wall of the casing 50 to penetrate the bottom of the casing 50, and the terminal 73 of the second electrode member 70 is led out of the casing 50 via a through-hole 50b which is formed at the bottom of the casing 50 and in close proximity to a side wall of the casing 50 which is opposite to the side wall in which the groove 50a is formed. The heat-conducting plate 52 which is positioned on the first electrode member 60 is supported on a step portion 57 which is integrally formed along inner surfaces of the side walls of the casing 50 in parallel with an opened surface of the casing 50. The heat-radiating member 90 is made of metal such as aluminium or the like and comprises a substantially U-shape body 93 and a pair of engaging arms 94 and 95 which depend from both sides of the U-shape body 93 in parallel with each other. The engaging arm 94 is provided at its tip end with an inwardly bent pawl 94a and the engaging arm 95 is likewise provided at its tip end with an inwardly bent pawl 95a. Correspondingly, the casing 50 is provided at each of its sides with a step portion 50g. The spacing between the engaging arms 94 and 95 is slightly less than the width of the casing 50. The U-shape heat-radiating member 90 is mounted with respect to the casing 50, which has the PTC thermistor 80 and the electrode members 60 and 70 received therein, in a manner to receive the casing 50 in the spacing between the engaging arms 94 and 95, the inwardly bent pawls 94a and 95a of which arms 94 and 95 are respectively engaged with the step portions 50g of the casing 50. As described above, the plate 71 of the second electrode member 70 is upwardly bowed to exhibit elasticity, so that the mounting of the heat-radiating member 90 with respect to the casing 50 may be carry out while tightly contacting the electrodes 81a and 81b of the PTC thermistor 80 with the plate 61 of the first electrode member 60 and the plate 71 of the second electrode member 70. The U-shape heat-radiating member 90 constructed as described above is adapted to receive in its opening 92 an upper end portion of a wick projecting from a reservoir which has liquid insecticide contained therein as will later be described in detail.

Figure 25:
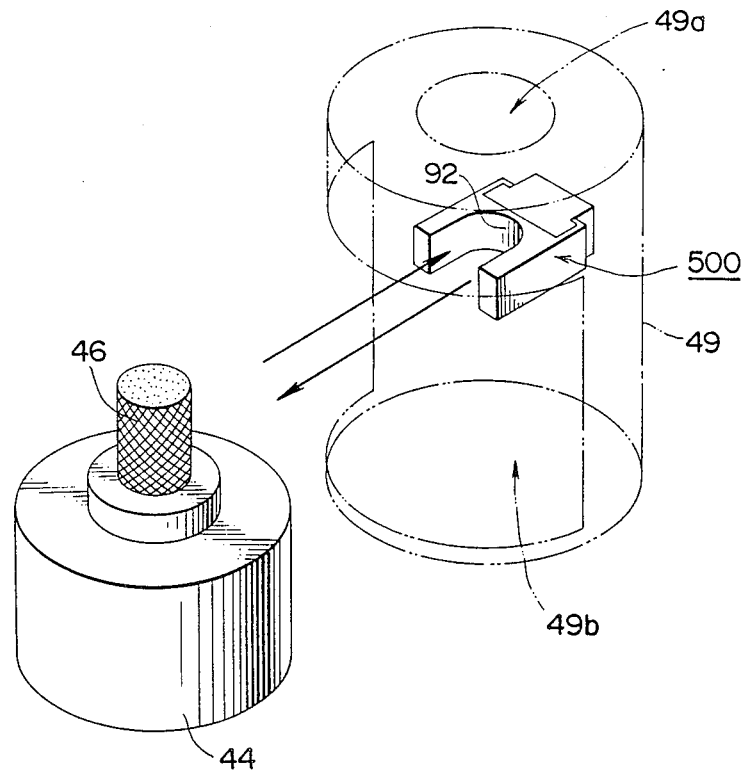
FIG. 25 is a schematic perspective view of assistance in explaining insertion of an upper end portion of a wick projecting from a reservoir into a U-shaped opening portion of a heat-radiating member incorporated into the PTC heating device of FIG. 24, and removal of the upper end portion of the wick from the U-shaped opening portion of the heat-radiating member.

FIG. 25 shows an electric mosquito destroyer which has the PTC heating device 500 of FIGS. 23 and 24 incorporated therein. In FIG. 25, a reference numeral 49 designates a case of the electric mosquito destroyer which has a through-hole 49a formed at its upper all and an opening 49b, a reference numeral 44 designates a reservoir having liquid insecticide contained therein and housed in the case 49, and a reference numeral 46 designates a wick. The reservoir 44 is adapted to be got in and out of the case 49 through the opening 49b of the case 49. The PTC heating device 500 of FIGS. 23 and 24 is held on the inner wall of the case 49 in a manner such that the opening 92 thereof faces toward the opening 49b of the case 49.

In the second embodiment, as described above, the heat-radiating member 90 is formed into a U-shape, so that getting of the upper end portion of the wick 46, projecting from the reservoir 44, into the opening 92 of the U-shaped heat-radiating member 90 and getting of the upper end portion of the wick 46 out of the opening 92 of the U-shaped heat-radiating member 90 is easily carried out. Further, as described above, the heat-radiating member 90 is provided with the engaging arms 94 and 95 which are adapted to be engaged with the step portions 50g of the casing 50, so that assembling operation of the PTC heating device 500 is easily carried out.

Figure 26:
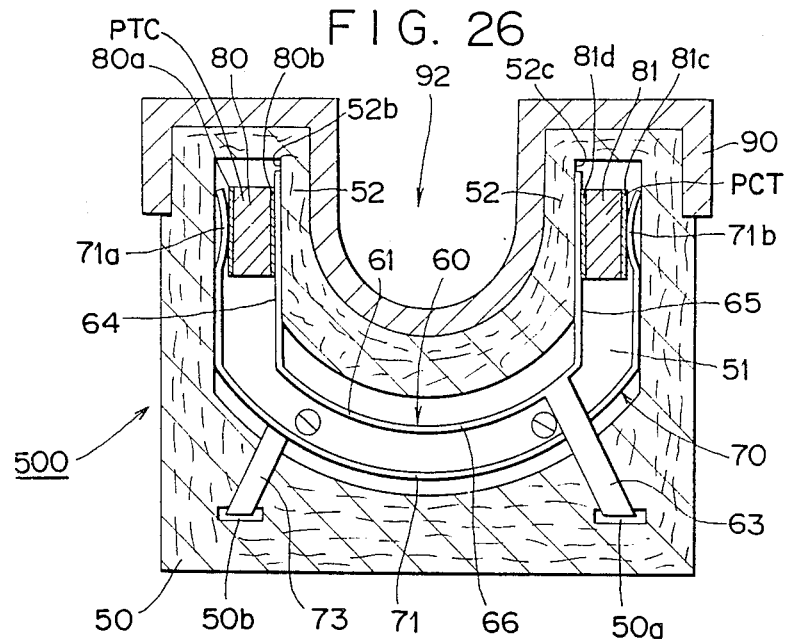
FIG. 26 is a sectional view of a PTC heating device according to a third embodiment of this invention.
Figure 27:
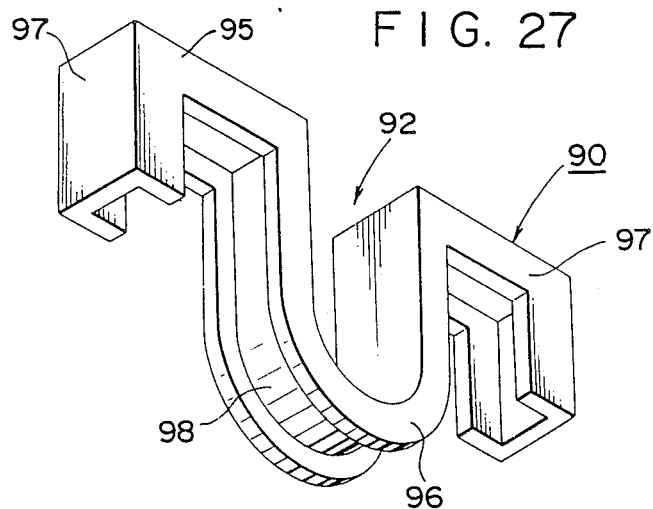
FIG. 27 is a perspective view showing a heat-radiating member which is incorporated in the PTC heating device of FIG. 26.

Referring to FIGS. 26 and 27, a PTC heating device 500 according to a third embodiment of this invention generally comprises a substantially U-shaped casing 50, first and second electrode members 60 and 70 which are received in the casing 50, a pair of substantially disc-like PTC thermistors 80 and 81 which are interposed between the first and second electrode members 60 and 70 and received in the casing 50, and a heat-radiating member 90 made of metal such as aluminum or the like.

The casing 50 is made of a heat-resistant electrically insulating material which has good thermal conductivity, for example, alumina porcelain or the like, and has a substantially U-shaped recess 51 formed therein in the same posture as the U-shaped casing 50 to form a hollow for receiving the first and second electrode members 60 and 70 and the PTC thermistors 80 and 81 therein. In the third embodiment of the present invention, a wall of the casing 50 surrounding a U-shaped opening of the casing 50 constitutes a heat-conducting portion 52.

The first electrode member 60 is made of an elastic and conductive material such as stainless steel and comprises a substantially U-shaped strip-like body 61 consisting of planar side sections 64 and 65 and a curved intermediate section 66 which interconnects the planar contact sections 64 and 65, and a lead-out terminal 63 extending outwardly from the curved section 66. The first electrode member 60 is received in the recess 51 of the casing 50 in a manner such that the planar contact sections 64 and 65 thereof are engaged with inner side surfaces 52b and 52c of the heat-conducting portion 52, respectively. The lead-out terminal 63 of the first electrode member 60 is led out of the casing 50 via a through-hole 50a which is formed at the casing 50.

The second electrode member 70 is made of the same material as the first electrode member 60 and comprises a substantially U-shaped strip-like body 71 and a lead-out terminal 73 extending outwardly from the U-shaped body 71 thereof. Both end portions 71a and 71b of the U-shaped body 71 are each curved inwardly of the U-shaped body 71, thereby exhibiting elasticity. The second electrode member 70 is received in the recess 51 of the casting 50 in a manner such that the end portion 71a and the end portion 71b thereof are opposed to the planar contact sections 64 and 65 of the first electrode member 60, respectively. The lead-out terminal 73 of the second electrode member 70 is led out of the casing 50 via a through-hole 50b which is formed at the casing 50.

The PTC thermistor 80 has a first electrode 80a and a second electrode 80b on its one flat surface and the other flat surface, respectively. This PTC thermistor 80 is interposed between the planar contact section 64 of the first electrode member 60 and the inwardly curved end portion 71a of the U-shaped body 71 of the second electrode member 70 in a manner such that the first electrode 80a and second electrode 80b thereof come into contact with the inwardly curved end portion 71a of the second electrode member 70 and the planar contact section 64 of the first electrode member 60, respectively, so that the PTC thermistor 80 is in close contact with the flat surface 52b of the heat-conducting portion 52 through the contact section 64 of the first electrode member 60 due to an elastic force of the inwardly curved end portion 71a of the second electrode memeber 70. Same as the PTC thermistor 80, the PTC thermistor 81 has a first electrode 81c and a second electrode 81b on its one flat surface and the other flat surface, respectively. The PTC thermistor 81 is interposed between the contact section 65 of the first electrode member 60 and the inwardly curved end portion 71b of the second electrode member 70 in a manner such that the first electrode 81c and second electrode 81d thereof come into contact with the inwardly curved end portion 71b of the second electrode member 70 and the planar contact section 65 of the first electrode member 60, respectively, so that the PTC thermistor 81 is in close contact with the flat surface 52c of the heat-conducting portion 52 through the contact section 65 of the first electrode member 60 due to an elastic force of the inwardly curved end portion 71b of the second electrode member 70.

The heat-radiating member 90 comprises a body 95 of a substantially inverted symbol-of-ohm shape as shown in FIG. 27. The body 95 comprises a substantially U-shape central portion 96 which protrudes outwardly, and an inverted L-shape portion 97 extending from each of both sides of the U-shape central portion 96. Also, the body 95 has a socket portion 98 formed along its side toward which the central portion 96 protrudes.

The PTC heating device 500 according to the third embodiment further includes a cover plate (not shown) which is made of a heat-resistant material and formed into a substantially U-shape. A size of a flat surface of the cover plate is the same as that of the casing 50. The cover plate is arranged on the casing 50 to close the recess 51 in which the electrode members 60 and 70 and the PTC thermistors 80 and 81 have been received. The U-shape assembly of the casing 50 and cover plate is fitted in the socket portion 98 of the heat-radiating member 90 at its U-shaped opening portion while receiving the protruding portion 96 of the heat-radiating member 90 in its opening.

In the PTC heating device 500 according to the third embodiment an upper end portion of a wick projecting from a reservoir having liquid insecticide contained therein is adapted to be got in an opening 92 of the heat-radiating 90.

In the first and third embodiments, the number of the PTC thermistors is two. However, it will be understood that the number of the PTC thermistors is not limited to two and still be within the scope of the invention.

While preferred embodiments of the invention have been described with a certain degree of particularity with reference to the drawings, obvious modifications and variations are possible in the light of the above teachings. It is therefore to be understood that within the scope of the appended claims, the invention may be practiced otherwise than as specifically described.

What is claimed is:

1. A PTC heating device for incorporation in electric vaporizer apparatus for heating and vaporizing liquid material, said electric vaporizer apparatus including storage means for containing said liquid material therein, a wick for drawing said liquid material from said storage means therethrough, and a case for housing said storage means therein, said wick having an elongated body for immersion in said liquid material in said storage means, one end portion of said elongated body projecting from said storage means, comprising:

a casing of heat-resistant electrically insulating material having a recess formed therein and a heat-conducting portion made of electrically insulating material having good thermal conductivity and formed integrally with said casing in a manner to vertically protrude from an outer surface of a bottom of said recess toward an opened side of said casing;

said heat-conducting portion having a vertical through-hole of a substantially cylindrical shape and a pair of planar surfaces formed on opposite portions of an outer surface of a wall surrounding said through-hole;

two substantially plate-like PTC thermistors each having a first electrode and a second electrode on respective first and second surfaces, thereof;

a first electrode member comprising a pair of spaced apart planar contact sections and an intermediate section interconnecting said spaced apart planar contact sections;

said first electrode member disposed in said recess of said casing with said planar contact sections having said heat-conducting portion interposed therebetween to form a surface of said heat-conducting portion;

each of said PTC thermistors disposed in said recess of said casing in a manner to be located on one of said planar contact sections of said first electrode member to form a surface contact with the planar contact section at said second electrode;

means on each of said planar contact sections of said first electrode member for preventing movement of a PTC thermistor in contact therewith;

a second electrode member formed of elastic material disposed in said recess of said casing and having means for engaging said respective first electrodes of said PTC thermistors on said planar contact sections of said first electrode member to elastically press said PTC thermistors onto respective planar surfaces of said heat-conducting portion through said planar contact section of said first electrode member;

a cover plate having a through-hole and located on said opened side of said casing;

means for mounting said PTC heating device with said case of said electric vaporizer extending therethrough and arranged on said cover plate;

said mounting means comprising a plate-like body having a through-hole formed therein, and a plurality of arms extending radially from peripheral portions of said platelike body;

a heat-radiating member of a substantially cylindrical shape mounted to said casing in a manner to be inserted through said through-hole of said mounting means, said cover plate and said heat-conducting portion, said cylindrical heat-radiating member having a bore for receiving said one end portion of said wick when said PTC heating device is incorporated in said electric vaporizer apparatus;

first cooperating means on said cover plate and said casing for preventing a rotational movement of said cover plate on said casing; and second cooperating means on said mounting means and said cover plate for preventing a rotational movement of said mounting means on said cover plate.

2. The PTC heating device defined in claim 1, wherein said casing is formed with two spaced through-holes in a bottom portion of said recess and wherein each of said first and second members has a lead-out terminal formed integrally therewith, said leadout terminal being projected outwardly through one of said through-holes of said casing.

3. The PTC heating device defined in claim 1, wherein said means for preventing movement of said PTC thermistors at each of said planar contact sections of said first electrode member comprises a plurality of tongue pieces located on each of said planar contact sections of said first electrode member in a manner to surround said PTC thermistors on each of said planar contact sections.

4. The PTC heating device defined in claim 3, wherein said tongue pieces are formed by bending edge portions of each of said planar contact sections of said first electrode member.

5. The PTC heating device defined in claim 1, wherein said first cooperating means comprises a plurality of projections formed integrally with said cover plate and project radially from peripheral portion of said cover plate, and a plurality of concavities corresponding in number to said plurality of projections of said cover plate and formed at said opened side of said casing by causing portions of a side wall of said casing to extend radially and form step portions along inner surfaces of said radially extending portions of said side wall, and wherein said cover plate is arranged on said casing in a manner such that said projections are engaged with said respective concavities of said casing.

6. The PTC heating device defined in claim 5, wherein two of said step portions of said casting have grooved formed therein, and each of said first and second electrode members has a lead-out terminal formed integrally therewith, said terminal being formed into a substantially L-shape and led out of said casing in a manner such that a horizontal portion of said L-shaped terminal engages one of said grooves and a vertical portion of said L-shaped terminal extends through a clearance between a tip end of one of said projections of said cover plate and a corresponding one of said concavities of said casing.

7. The PTC heating device in claim 6, wherein said L-shaped terminal of each of said first and second electrode members has a substantially quadrant-shaped reinforcement means formed by cutting out a part of a corner portion of said L-shaped terminal to curve the same inwardly of said corner portion.

8. The PTC heating device defined in claim 1, wherein said second cooperating means comprises a projection formed by causing said plate-like body of said mounting means to be slightly projected toward said cover plate on which said mounting means is arranged from a plane of said arms of said mounting means, and a depression formed in said cover plate, said depression of said cover plate and said arms of said mounting means are engaged with respective ones of said radially extending portions of said depression of said cover plate.

9. The PTC heating device defined in claim 1, wherein said second electrode member comprises a strip-like body curved into a substantially C-shape, and said means engaging with said respective first electrode of said PTC thermistors on said planar contact sections of said first electrode member including a forked portion formed at each end portion of said substantially C-shaped body of said second electrode member, said formed portion being curved inwardly of said substantially C-shaped body, to elastically press said PTC thermistors onto said respective planar surfaces of said heat-conducting portion through said planar contact sections of said first electrode member.

10. The PTC heating device defined in claim 1, wherein said cover plate is sealed to said casing by means of one of sealing compounds and adhesives.

11. In a PTC heating device for incorporation in electric vaporizer apparatus for heating and vaporizing liquid material, said electric vaporizer apparatus including a case, storage means for containing said liquid material housed in said case, said case having an opening for allowing said storage means to be received in and removed from said case, and a wick, for drawing said liquid material from said storage means therethrough, said wick having an elongagted body for immersion in said liquid material in said storage means, one end portion of said elongated body projecting from said storage means, said PTC heating device including a substantially plate-like PTC thermistor having first and second electrodes on respective first and second surfaces thereof, a first and a second electrode member comprising a pair of plates between which said PTC thermistor is interposed, said first electrode member including a first substantially planar contact section in contact with said first electrode of said PTC thermistor, said second electrode member including a second contact section in engagement with said second electrode of said PTC thermistor; a casing of heating-resistant electrically insulating material having a recess formed therein, said PTC thermistor and said first and second electrode members being disposed within said recess; a heat-conducting member made of heat-resistant, electrically insulating material having good thermal conductivity arranged on said first electrode member; and a heat-radiating member arranged on said heat-conducting member for heating and vaporizing said liquid material, drawn up from said storage means by said wick, the improvement comprising:

said heat-radiating member taking the form of a substantially U-shaped body having a substantially U-shaped opening for receiving said one end portion of said elongated body of said wick projecting from said storage means when said PTC heating device is incorporated in said electric vaporizer apparatus enabling said one end portion of said wick projecting from said storage means to be readily removed from said opening portion of said heat-radiating member when said liquid material contained in said storage means is consumed in use of said electric vaporizer apparatus and said storage means is removed from said case of said electric vaporizer apparatus for replacement.

12. The PTC heating device defined in claim 11, wherein said body of said heat-radiating member includes a pair of engaging arms formed integrally therewith in a manner to extend from both sides of said body of said heat-radiating member in opposite directions to said U-shaped opening and said heat-radiating member is arranged in close contact on said heat-conducting member to dispose the sides of said casing within said engaging arms.

13. In a PTC heating device incorporated in electric vaporizer apparatus for heating and vaporizing liquid material, said electric vaporizer apparatus including a case, storage means for containing said liquid material housed in said case, said case having an opening for allowing said storage means to be received in and removed from said case, and a wick for drawing said liquid material from said storage means therethrough, said wick having an elongated body for immersion in said liquid material in said storage means, and at least one end portion of said elongated body projecting from said storage means, said PTC heating device including two substantially plate-like PTC thermistors each having a first electrode and a second electrode on respective first and second surfaces thereof; first and second electrode members between which said PTC thermistors are disposed; a casing of heat-resistant electrically insulating material having a recess formed therein, said PTC thermistors and said first and second electrode members being disposed within said recess; a cover plate of electrically insulating material located on said casing having said PTC thermistors and said electrode members disposed therein, said cover plate being positioned to close said recess of said casing; and a heat-radiating member for heating and vaporizing said liquid material drawn up from said storage means by said wick, the improvement comprising:

said casing being formed into a substantially U-shape;

said recess being formed into a substantially U-shape corresponding to that of said casing;

said first electrode member taking the form of a substantially U-shaped strip-like body having a substantially planar contact section at each side thereof, said first electrode member being disposed in said recess of said casing in a manner causing said planar contact sections of said strip-like body to respectively engage the inner surfaces of both side portions of a wall of said casing surrounding an open portion of said casing;

each of said PTC thermistors being disposed in said recess of said casing in a manner to contact one of said planar contact sections of said first electrode member at said second electrode thereof;

said second electrode member being formed of elastic material having a substantially U-shaped strip-like body and a contact section at each side thereof, said second electrode member being disposed in said recess of said casing in a manner to surround said first electrode member and contacting said first electrodes of said PTC thermistors to elastically press said PTC thermistors onto side portions of said wall of said casing surrounding said open portion of said U-shaped casing through said first electrode member;

said cover plate being formed into a substantially U-shape and located on said casing having said electrode members and said PTC thermistors disposed in the recess thereof; and said heat-radiating member taking the form of a body in substantially the shape of an inverted Ohm symbol having said one end portion of said elongated body of said wick projecting from said storage means disposed in an open central portion thereof when said PTC heating device is incorporated in said electric vaporizer apparatus, a socket portion being formed along said inverted Ohm symbol body, said heat radiating member being mounted with respect to an assembly of said casing, and said cover plate in a manner to cause said socket portion to receive the side of said U-shaped portion of said assembly therein;

wherein when said liquid material contained in said storage means is removed from said case of said electric vaporizer apparatus for replacement, said one end portion of said wick, projecting from said storage means, can readily be removed from said open portion of said heat-radiating member.

* * * * *

UNITED STATES PATENT AND TRADEMARK OFFICE
CERTIFICATE OF CORRECTION

PATENT NO. : 4,874,924
DATED : October 17, 1989
INVENTOR(S) : SHINOBU YAMAMOTO ET AL.

It is certified that error appears in the above-identified patent and that said Letters Patent is hereby corrected as shown below:

Title page: Item [73] should read as follows:

[73] Assignees: TDK Inc.; Fumakilla Ltd., both of Tokyo, Japan

Signed and Sealed this

Sixteenth Day of April, 1991

Attest:

HARRY F. MANBECK, JR.

Attesting Officer

Commissioner of Patents and Trademarks